United States Patent
Hohlig et al.

(10) Patent No.: US 12,359,206 B2
(45) Date of Patent: Jul. 15, 2025

(54) CXCL8 BINDING NUCLEIC ACIDS

(71) Applicant: Aptarion Biotech AG, Berlin (DE)

(72) Inventors: Kai Hohlig, Berlin (DE); Axel Vater, Berlin (DE); Werner Purschke, Berlin (DE); Dirk Zboralski, Berlin (DE); Christian Maasch, Berlin (DE)

(73) Assignee: Aptarion Biotech AG, Berlin (DE)

( * ) Notice: Subject to any disclaimer, the term of this patent is extended or adjusted under 35 U.S.C. 154(b) by 1095 days.

(21) Appl. No.: 17/293,065

(22) PCT Filed: Nov. 12, 2019

(86) PCT No.: PCT/EP2019/000312
§ 371 (c)(1),
(2) Date: May 12, 2021

(87) PCT Pub. No.: WO2020/098968
PCT Pub. Date: May 22, 2020

(65) Prior Publication Data
US 2021/0403913 A1    Dec. 30, 2021

(30) Foreign Application Priority Data
Nov. 12, 2018 (EP) .................... 18205750

(51) Int. Cl.
*C12N 15/115* (2010.01)
*C12Q 1/6876* (2018.01)
*G01N 33/68* (2006.01)

(52) U.S. Cl.
CPC .......... *C12N 15/115* (2013.01); *C12Q 1/6876* (2013.01); *G01N 33/6869* (2013.01); *C12N 2310/16* (2013.01); *C12N 2310/351* (2013.01); *G01N 2333/5421* (2013.01)

(58) Field of Classification Search
CPC .............. C12N 15/115; C12N 2310/16; C12N 2310/351
See application file for complete search history.

(56) References Cited

U.S. PATENT DOCUMENTS 9,163,243 B2    10/2015    Schulzchen et al.
9,518,265 B2    12/2016    Hohlig et al.

FOREIGN PATENT DOCUMENTS

WO    2014/137141    9/2014
WO    WO 2018172556    * 3/2018

OTHER PUBLICATIONS

English language translation of Russia Office Action dated Jun. 2, 2023.
Sonksen & Sonksen. "Insulin . . . disease," J Anesthesia 85(1)69-79, 2000 sent by Russia PO Jun. 22, 2023.
Sung et al., "Inhibition . . . interleukin-8," Biomat 35(1)578-589, 2013.
Kratschmer et al., "Effect . . . Serum," Nucl Acid Therap 27(6)335-344, 2017.

* cited by examiner

*Primary Examiner* — Brian Whiteman
(74) *Attorney, Agent, or Firm* — MDIP LLC

(57) ABSTRACT

The present invention is related to an L-nucleic acid molecule capable of binding to human CXCL8, wherein the L-nucleic acid molecule comprises a central stretch of nucleotides, wherein the central stretch of nucleotides comprises a nucleotide sequence of 5'-GG A AGU ACGUGGA AAGCCRA(Xu)RAGUGUGUCCCG-3'[SEQ. ID. NO: 27], wherein Xu is U or absent.

21 Claims, 9 Drawing Sheets
Specification includes a Sequence Listing.

Sequences of CXCL8 binding nucleic acids

| Name | nt | Sequence: 5'-3' | D-Aptamer Pull-down $K_d$ (nM) |
|---|---|---|---|
| 315-H9-001 | 45 | GCUGAC GGAAGUACGUGGAAAGCCAAUGAGUGUCCCG GUCAGC | 2.6 |
| 315-F11-001 | 45 | GCUGAC GGAAGUACGUGGAAAGCCGAUGAGUGUCCCG GUGAGC | 12.5 |
| 315-F8-001 | 44 | GCUGAC GGAAGUACGUGGAAAGCCGA-AAGUGUCCCG GUCAGC | 1.5 | nt: number of nucleotides; bold: terminal nucleotides that may hybridize to each other; central stretch: nucleotides which may mainly comprise a CXCL8-binding motif, *variable position*. Dissociation constant $K_d$ of D-aptamers, measured by competition pull-down binding assay.

FIGURE 1

Sequences of CXCL8 binding nucleic acids: Truncated derivatives of 315-F8-001

| Name | nt | Sequence: 5'-3' | D-Aptamer Pull-Down R | D-Aptamer Pull-Down $K_d$ (nM) | L-Aptamer SPR $K_d$ (nM) 25°C | L-Aptamer SPR $K_d$ (nM) 37°C |
|---|---|---|---|---|---|---|
| 315-F8-001 | 44 | GCUGAC GGAAGUACGUGGAAAGCCGAAAGUGUCCCG GUCAGC | = | 1.5 | 0.22 | 0.68 |
| 315-F8-002 | 42 | CUGAC GGAAGUACGUGGAAAGCCGAAAGUGUCCCG GUCAG | + | 1.1 | 0.22 | 0.75 |
| 315-F8-002-PEG | 42 | PEG-CUGAC GGAAGUACGUGGAAAGCCGAAAGUGUCCCG GUCAG | | | 0.21 | 0.81 |
| 315-F8-003 | 40 | UGAC GGAAGUACGUGGAAAGCCGAAAGUGUCCCG GUCA | < | | | |
| 315-F8-004 | 38 | GAC GGAAGUACGUGGAAAGCCGAAAGUGUCCCG GUC | < | | | |
| 315-F8-005 | 42 | GUGAC GGAAGUACGUGGAAAGCCGAAAGUGUCCCG GUCAC | = | | | |
| 315-F8-006 | 40 | GGAC GGAAGUACGUGGAAAGCCGAAAGUGUCCCG GUCC | < | | | |
| 315-F8-007 | 40 | GCAC GGAAGUACGUGGAAAGCCGAAAGUGUCCCG GUGC | < | | | |
| 315-F8-008 | 40 | GGUC GGAAGUACGUGGAAAGCCGAAAGUGUCCCG GACC | < | | | |
| 315-F8-009 | 40 | UGGC GGAAGUACGUGGAAAGCCGAAAGUGUCCCG GCCA | < | | | | nt: number of nucleotides; bold: terminal nucleotides that may hybridize to each other; central stretch: nucleotides which may mainly comprise a CXCL8-binding motif. D-Aptamer Competition pull-Down CXCL8 binding assay: Ranking (R) and dissociation constant Kd of D-aptamers measured by competition pull-down assay; =, similar affinity as reference (315-F8-001); <, lower affinity than reference; +, higher affinity compared to reference. Dissociation constant Kd of L-aptamers binding to CXCL8 measured by SPR.

FIGURE 2

CXCL8 binding L-aptamer 315-F8-002
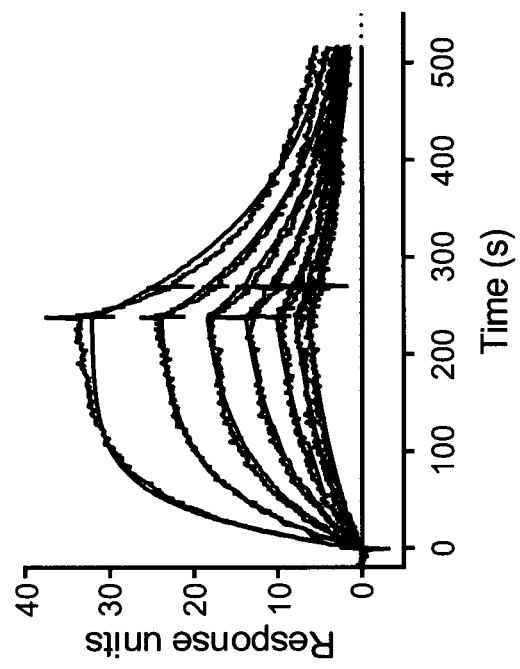
A
$k_a = 8.4 \times 10^6 \, / \, \text{Ms}; \; k_d = 1.9 \times 10^{-3} \, / \, \text{s}$
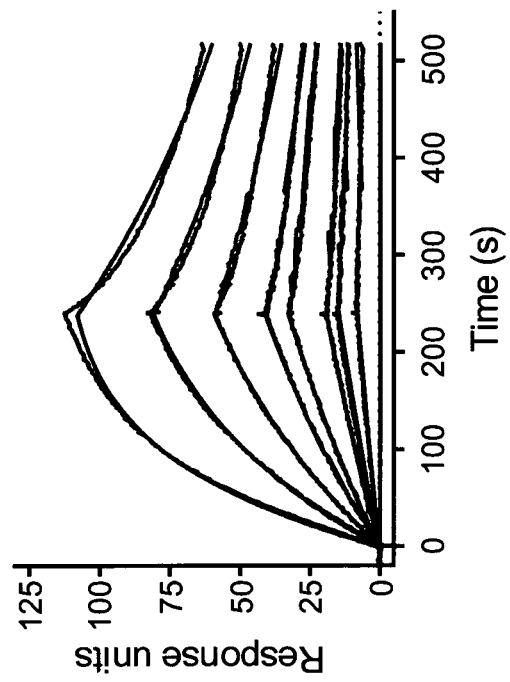
B
$k_a = 1.7 \times 10^7 \, / \, \text{Ms}; \; k_d = 1.3 \times 10^{-2} \, / \, \text{s}$
FIGURE 4

CXCL8 binding L-aptamer 315-F8-002-PEG
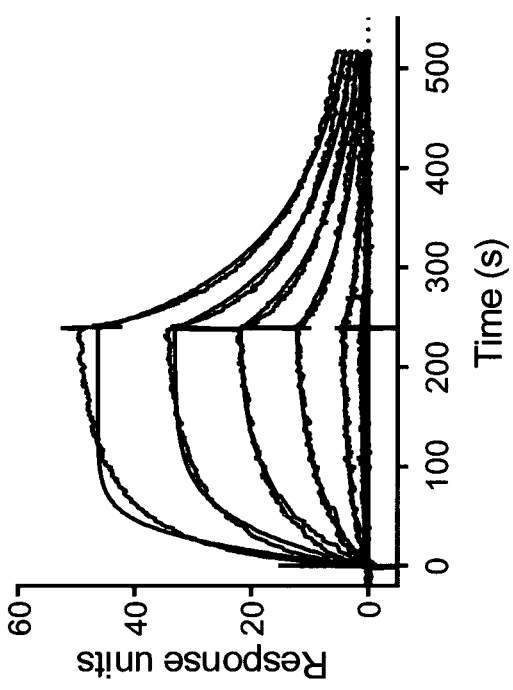
A
$k_a = 1.1 \times 10^7 / \text{Ms}; k_d = 2.2 \times 10^{-3} / \text{s}$
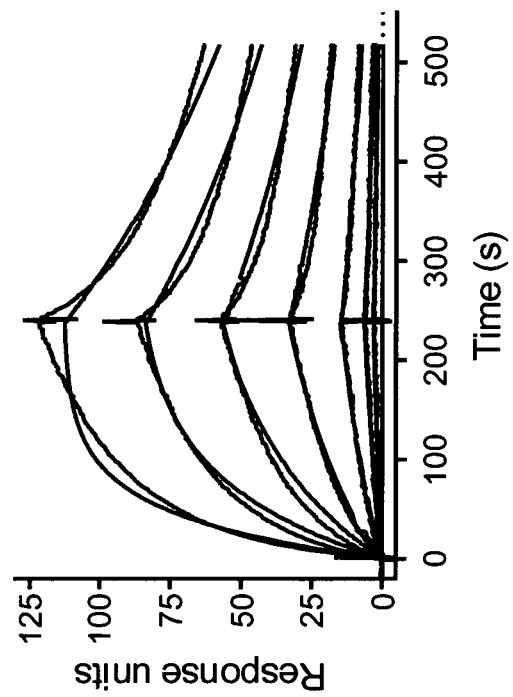
B
$k_a = 1.8 \times 10^7 / \text{Ms}; k_d = 1.5 \times 10^{-2} / \text{s}$
FIGURE 5

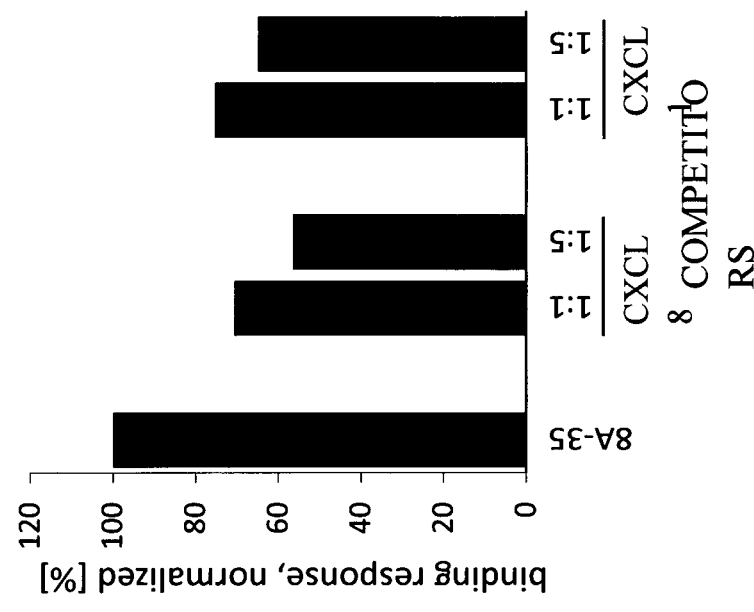
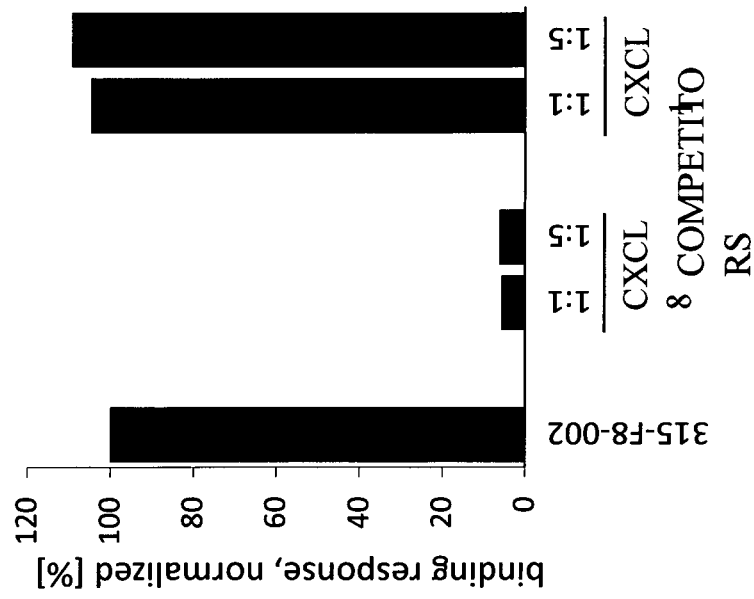
FIGURE 9

CXCL8 BINDING NUCLEIC ACIDS

The present invention is related to a nucleic acid molecule capable of a binding to CXCL8, the nucleic acid molecule for use in a method for the treatment and/or prevention of a disease, the nucleic acid molecule for use in a method for detecting CXCL8, the nucleic acid molecule for manufacture of a detection means or a biosensor, a pharmaceutical composition comprising the nucleic acid molecule, use of the nucleic acid molecule for the manufacture of a medicament, use of the nucleic acid molecule for the manufacture of a diagnostic, a diagnostic means or a biosensor, use of the nucleic acid molecule for the detection of CXCL8, a kit comprising the nucleic acid molecule, a method for the detection of CXCL8 using the nucleic acid molecule, a complex comprising the nucleic acid molecule, a method for the screening of an antagonist of an activity mediated by CXCL8 using the nucleic acid molecule, and a method for the detection of the nucleic acid molecule.

CXCL8 (UniProtKB/Swiss-Prot P10145, IL8_HUMAN; SEQ ID NO: 2), also known as interleukin 8 (abbr. IL-8), neutrophil-activating protein 1 (abbr. NAP-1), monocyte-derived neutrophil chemotactic factor (abbr. MDNCF), or granulocyte chemotactic protein 1 (abbr. GCP-1), is a small basic protein that belongs to a subfamily of CXC chemokines with pro-inflammatory and pro-angiogenic properties characterized by a glutamate-leucine-arginine (abbr. ELR) motif at the N-terminus. ELR-positive chemokines CXCL1 (also known as growth-regulated alpha protein, Gro-alpha, Melanoma growth stimulatory activity, MGSA, or NAP-3), CXCL2 (also known as Gro-beta or Macrophage inflammatory protein 2-alpha, MIP2-alpha), CXCL3 (also known as Gro-gamma or MIP2-beta), CXCL5 (also known as epithelial-derived neutrophil-activating protein 78, ENA-78, or small-inducible cytokine B5), CXCL6 (also known as chemokine alpha 3, CKA-3, granulocyte chemotactic protein 2, GCP-2, or small-inducible cytokine B6), CXCL7 (also known as platelet basic protein, PBP, leukocyte-derived growth factor, LDGF, macrophage-derived growth factor, MDGF, or small-inducible cytokine B7), and CXCL8 are agonists of the receptor CXCR2 (also known as IL8RB, IL8R type 2, CD182, CDw128b, or GRO/MGSA receptor). CXCL6, CXCL7, and CXCL8 are agonists of the receptor CXCR1 (also known as IL8RA, IL8R type 1, CD181, or CDw128a). CXCL8 binds to receptors CXCR1 and CXCR2 with similar affinities of about 4 nM. CXCL8 binding to CXCR1/2 triggers Gui-dependent signaling pathways and, for example, induces neutrophil migration, degranulation and oxidative burst. Receptor sensitivity can be regulated by phosphorylation, beta-arrestin recruitment and receptor internalization (Ha, Theranostics 2017). CXCL7 has the highest homology to CXCL8 with 33 identical amino acids. CXCL8 from non-human primates (*macaca* mulata, cynomolgus monkey) share 95% identity (73 of 77 amino acids identical) with human CXCL8. There is no ortholog of CXCL8 in mice and rats.

CXCL8 is secreted by different cell types including monocytes, macrophages, fibroblasts, endothelial and epithelial cells in response to, for example, pathogen-associated molecular pattern (abbr. PAMP) molecules (e.g. LPS), pro-inflammatory mediators (e.g. IL-1, IL-6 and TNF-a), hypoxia, reactive oxygen species or environmental stress factors (e.g. cigarette smoke) (Ha, Theranostics 2017). CXCL8 acts as a chemotactic and activating cytokine for neutrophils and monocytes and plays an important physiological role in host defense.

CXCL8 is used as a biomarker for diagnosis, disease status, prognosis and therapeutic efficacy in infectious diseases with elevated CXCL8 levels having been described in viral infections (e.g. respiratory syncytial virus, herpes simplex virus, hepatitis virus B and C, human cytomegalovirus), bacterial infection (e.g. Stretptococcus *pneumoniae* and *Mycobacterium tuberculosis*) and fungal infection (e.g. *Candida albicans* and *Aspergillus fumigatus*). In pediatric respiratory syncytial virus (abbr. RSV) infection CXCL8 plasma levels correlate with disease severity. Thus, CXCL8 can serve as a biomarker to assess severity of RSV infection and guide clinical management. Combination with other immunological biomarkers, namely lymphocyte counts and CCL5 plasma levels, enhances accuracy (Brand, Pediatr Res 2013). Further examples for the use of CXCL8 as a biomarker in infectious diseases are neonatal sepsis (Zhou, PLoS One 2015), bacterial meningitis (Yao, Int J Clin Exp Med 2015), pneumonia (Morris, Thorax 2009), and neurosyphilis (Wang, Sci Rep 2016). CXCL8 may also be used as a biomarker in inflammatory diseases, including chronic prostatitis, acute pyelonephritis, cystic fibrosis and various autoimmune diseases (Shahzad, Int Arch Med 2010). In cancer patients, CXCL8 levels correlate with tumor burden and worse outcome (Sanmamed, Clin Cancer Res 2014). For example, CXCL8 correlates with shorter survival in breast cancer (Fang, Anticancer Res 2017) and pancreatic cancer (Chen, World J Gastroenterol 2012) and pediatric sarcoma (Highfill, Sci Transl Med 2014). In melanoma, elevated baseline CXCL8 levels correlate with non-responsiveness to anti-CTLA 4/chemotherapy combination treatment and worse patient outcomes (Jamal, J Immunother Cancer 2017).

CXCL8 and its receptors are implicated in the pathogenesis of several inflammatory diseases including inflammatory diseases of the respiratory system (e.g. chronic obstructive pulmonary disorder, acute respiratory distress syndrome, asthma, cystic fibrosis, pulmonary fibrosis), inflammatory diseases of the skin (e.g. neutrophilic dermatoses, psoriasis, bullous pemphigoid), autoimmune diseases (e.g. inflammatory bowel diseases, ulcerative colitis, multiple sclerosis, rheumatoid arthritis), inflammatory neurological diseases (e.g. neuro-sweet disease, Alzheimer disease), ischemic diseases (e.g. stroke, myocardial infarction, cerebral ischemia and infarction) and other inflammatory diseases (e.g. atherosclerosis) (Ha, Theranostics 2017; Russo, Expert Rev Clin Immunol 2014). The potential of inhibiting CXCL8 for the treatment of such inflammatory diseases is supported by animal disease models. For example, in rabbits, anti-CXCL8 antibody administration improved LPS-induced dermatitis, LPS-induced pleurisy, LPS/IL-1-induced arthritis, IC-type glomerulonephritis, acute lung injury, and lung reperfusion injury (Bao, Int Immunopharmacol 2010; Harada, J Leukoc Biol 1994). CXCR1/2 blockade reduced ischemic brain injury in a rat model (Garau, Cytokine 2005).

CXCL8 is implicated in the development, progression and treatment-resistance of human cancers including lung cancer, colon cancer, prostate cancer, pancreatic cancer, breast cancer, ovarian cancer, and melanoma, and promotes tumor growth and metastasis (Brat, Neuro Oncol 2005; Ha, Theranostics 2017; Koch, Science 1992; Li, Angiogenesis 2005; Liu, Cytokine Growth Factor Rev 2016; Xu, Oncol Res 2000). Mechanisms of cancer promotion by CXCL8 include the stimulation of angiogenesis, cancer stem cell self-renewal, epithelial-to-mesenchymal transition, and the generation of an immunosuppressive tumor microenvironment (Ginestier, J Clin Invest 2010; Visvader, Nat Rev Cancer 2008; David, Vaccines 2016). The potential of inhibiting CXCL8 for the treatment of human cancer is supported by animal disease models. For example, CXCL8 knockdown reduces the growth of chemotherapy-resistant ovarian cancer cells (Merritt, J Natl Cancer Inst 2008). Inhibition of CXCL8 augments anti-angiogenic responses elicited by docetaxel in ovarian and prostate cancer models (Campbell, Pharmaceuticals 2013). CXCL8 overexpression in phosphatase and tensin homolog (PTEN) insufficient tumors enhances cancer cell viability and contribute to the development of treatment-resistant tumours (Campbell, Pharmaceuticals 2013; Maxwell, Eur Urol 2013; Maxwell, Oncotarget 2014). Inhibition of CXCL8 signaling sensitizes PTEN-deficient as well as p53-mutant cancer cells to DNA-damaging agents, anti-metabolites or androgen receptor-targeting strategies (Campbell, Pharmaceuticals 2013). CXCR2 blockade enhanced the efficacy of immune checkpoint inhibitor anti-PD-1 in mouse models of rhabdomyosarcoma and pancreatic ductal adenocarcinoma (Highfill, Sci Transl Med 2014; Steele, Cancer Cell 2016).

Several compounds targeting CXCL8 or one or both the respective receptors CXCR1 and CXCR2 are known and were successfully tested in in vivo models. Some of them have been further tested in clinical trials. Antagonists of CXCR1 and/or CXCR2, namely reparixin, ladarixin, danirixin, navarixin, SX-682 and AZD-5069 are tested in clinical trials for pancreatic islet transplantation, organ transplantation, type 1 diabetes, COPD, asthma, bronchiectasis, psoriasis, bullous pemphigoid, and cancer. CXCR1/2 antagonist reparixin is further clinically tested in patients with metastatic triple-negative breast cancer. CXCR2 antagonist AZD-5069 is tested in combination with anti-PD-L1 durvalumab or chemotherapies in solid cancers.

Although sharing the receptors CXCR1 and CXCR2, ELR-positive chemokines have distinct expression patterns, in vivo distribution (extracellular matrix binding properties) and mechansisms of interaction with the receptors (Feniger-Barish, Cytokine 1999; Sawant, Sci Rep 2016). The respective physiological functions of the different ELR-positive chemokine family members are poorly understood. Thus, selective inhibition of disease promoting CXCL8 will potentially be more effective in disease treatment and reduce the risk of side effects compared to the broad blockade of CXCR1/CXCR2 blockade. For example, CXCL8 but not CXCL1 is required for the maintenance of cancer stem cells (Liotti F et al., Stem Cells 2017; 35:135-146). In infection, chemokines have overlapping activities. Consequently, a broad inhibition of ELR-positive chemokines (e.g. simultaneous inhibition of CXCL8 and CXCL1) could be associated with an enhanced risk of infection (Yung S C and Murphy P M; frontiers in Immunology, September 2012, vol. 3, Art. 276) CXCRT/2 ligands share a common N-terminal ELR motif which can serve as a binding epitope (described in U.S. Pat. No. 9,783,605). The presence of this shared structural feature in CXCRT/2 ligands CXCL1, CXCL2, CXCL3, CXCL5, CXCL6, CXCL7 and CXCL8 is a challenge when attempting to identify a compound that will selectively bind and inhibit CXCL8 without interfering with other ELR-positive chemokines.

Antibodies binding to CXCL8 but not to ELR-positive chemokines CXCL1 (also known as growth-regulated protein alpha, GRO-alpha) and CXCL2 (also known as growth-regulated protein beta, GRO-beta) have been identified (Skov, J Immunol 2008). CXCL8-specific monoclonal antibodies have so far failed to show efficacy in clinical trials which may be associated with the pharmacological properties of this substance class, including pharmacokinetic profile, biodistribution and elimination. For example, high chemokines production rates may result in a rapid saturation of therapeutic antibodies and insufficient efficacy with routinely used long dosing intervals. Futhermore, antibodies might potentially not interfere with the binding of chemokines to glycosaminoglycans, resulting in a lack of chemokine gradient destruction and insufficient inhibition of leukocyte migration and extravasation. Nucleic acids preferentially bind to the glycosaminoglycan-binding sites of proteins (Oberthur, Nat Commun 2015). Thus, other substance classes, like nucleic acids, could be superior for the therapeutic targeting of CXCL8.

Nucleic acids are sensitive to degradation by enzymes (nucleases) present in body fluids. This lack of biostability hampers the manufacture of nucleic acid-based medicaments for the treatment of a human as well as the manufacture of nucleic acid-based diagnostic agents for the identification and/or treatment of a disease. Chemical modifications can increase the stability of nucleic acids but may be insufficient to provide sufficient stability for use a medicament. For example, a nucleic acid with 2'-fluoro modified pyrimidines showed a plasma half-life comparable to an all-DNA nucleic acid and 2'-O-methyl modifications were required to achieve long half-lifes (Kratschmer, Nucleic Acid Ther 2017). Macugen, the first aptamer approved for therapeutic use, is stabilized by a combination of 2'-fluoro-pyrimidines, 2'-O-methyl-purines and a 3'-cap. Moreover, chemical modifications may come with an increased risk of side effects when used for the manufacture of a medicament. In contrast, nucleic acids of non-natural L-configuration are highly biostable and have been shown to be safe, well-tolerated and efficacious in clinical trials (Ludwig, Leukemia 2017; Menne, Nephrol Dial Transplant 2016).

CXCL8-binding 2'-fluoro pyrimidine RNA-aptamers have previously been described (Sung, Biomaterials 2014). However, in functional assays, the high binding affinity of one of the described aptamers, aptamer 8A-35, has not translated into improved functionality with inhibiting CXCL8-induced neutrophil migration with IC50>125 nM. Semiquantitative analysis suggested no or low binding of an precursor aptamer to ELR-positive chemokines CXCL1 (also known as GRO-alpha) and CXCL2 (also known as GRO-beta).

The problem underlying the present invention is to provide a nucleic acid molecule, preferably an L-nucleic acid, which specifically interacts with CXCL8, preferably does not specifically interact with other ELR-positive chemokines, and more preferably does not with ELR-positive chemokines that bind to the receptors CXCR1 and/or CXCR2.

Another problem underlying the present invention is to provide for a nucleic acid molecule, preferably an L-nucleic acid molecule, which binds to CXCL8 with high affinity, thereby allowing to effectively inhibit CXCL8-stimulated chemotaxis, preferably with an inhibitory constant in the single digit nanomolar range, more preferably in the picomolar range.

A further problem underlying the present invention is to provide a nucleic acid molecule, preferably an L-nucleic acid molecule, for the manufacture of a medicament for the treatment of a human, and/or non-human diseases, whereby the disease is characterized by CXCL8 being either directly or indirectly involved in the pathogenetic mechanism of such disease, preferably at least to the extent that antagonizing or inhibiting CXCL8 results in a therapeutic effect.

A still further problem underlying the present invention is to provide a nucleic acid molecule, preferably an L-nucleic acid molecule, for the manufacture of a diagnostic agent for the identification, diagnosis and/or treatment of a disease, whereby the disease is characterized by CXCL8 being either directly or indirectly involved in the pathogenetic mechanism of such disease.

These and other problems underlying the present invention are solved by the subject matter of the attached independent claims. Preferred embodiments may be taken from the dependent claims.

More specifically, the problem underlying the present invention is solved in a first aspect by an L-nucleic acid molecule capable of binding to human CXCL8, wherein the L-nucleic acid molecule comprises a central stretch of nucleotides, wherein the central stretch of nucleotides comprises a nucleotide sequence of

[SEQ. ID. NO: 27]
5'-GGAAGUACGUGGAAAGCCRA($X_U$)RAGUGUGUCCCG-3', wherein $X_U$ is U or absent.

More specifically, the problem underlying the present invention is solved in a second aspect by an L-nucleic acid molecule of the first aspect, including any embodiment thereof, for use in a method for the treatment and/or prevention of a disease More specifically, the problem underlying the present invention is solved in a third aspect by an L-nucleic acid molecule of the first aspect, including any embodiment thereof, for use in a method for detecting CXCL8.

More specifically, the problem underlying the present invention is solved in a fourth aspect by an L-nucleic acid molecule of the first aspect, including any embodiment thereof, for manufacture of a detection means or a biosensor.

More specifically, the problem underlying the present invention is solved in a fifth aspect by a pharmaceutical composition comprising an L-nucleic acid molecule as according to the first aspect, including any embodiment thereof, and optionally a further constituent, wherein the further constituent is selected from the group comprising a pharmaceutically acceptable excipient, a pharmaceutically acceptable carrier and a pharmaceutically active agent.

More specifically, the problem underlying the present invention is solved in a sixth aspect by the use of an L-nucleic acid molecule according to the first aspect, including any embodiment thereof, for the manufacture of a medicament.

More specifically, the problem underlying the present invention is solved in a seventh aspect by the use of an L-nucleic acid molecule according to the first aspect, including any embodiment thereof, for the manufacture of a diagnostic, a diagnostic means or a biosensor.

More specifically, the problem underlying the present invention is solved in an eighth aspect by the use of an L-nucleic acid molecule according to the first aspect, including any embodiment thereof, for the detection of CXCL8, preferably human CXCL8.

More specifically, the problem underlying the present invention is solved in a ninth aspect by a kit for the detection of CXCL8, wherein the kit comprises an L-nucleic acid molecule according to the first aspect, including any embodiment thereof, and at least an instruction leaflet or a reaction vessel.

More specifically, the problem underlying the present invention is solved in a tenth aspect by a method for the detection of CXCL8 using the L-nucleic acid as defined according to the first aspect, including any embodiment thereof, in a sample, wherein the method comprises the steps of:

a) providing a sample with unknown concentration of CXCL8;
b) bringing the sample or a dilution thereof in contact with a diagnostic, diagnostic means or biosensor as defined in the seventh aspect, including any embodiment thereof;
c) measuring the signal with a diagnostic, diagnostic means or biosensor as defined in the seventh aspect, including any embodiment thereof;
d) optionally, comparing the signal with a reference;
optionally, the concentration of CXCL8 in a sample with unknown CXCL8 concentration is determined by comparison with signals obtained from at least one sample with known CXCL8 concentration, preferably the at least one sample with a known CXCL8 concentration is subject to steps b) to c).

More specifically, the problem underlying the present invention is solved in an eleventh aspect by a complex comprising an L-nucleic acid molecule according to the first aspect, including any embodiment thereof, and CXCL8, wherein preferably the complex is a crystalline complex.

More specifically, the problem underlying the present invention is solved in a twelfth aspect by a method for the screening of an antagonist of an activity mediated by CXCL8 comprising the following steps:
providing a candidate antagonist of the activity mediated by CXCL8,
providing an L-nucleic acid molecule according to the first aspect, including any embodiment thereof,
providing a test system which provides a signal in the presence of an antagonist of the activity mediated by CXCL8, and
determining whether the candidate antagonist of the activity mediated by CXCL8 is an antagonist of the activity mediated by CXCL8.

More specifically, the problem underlying the present inventin is solved in a $13^{th}$ aspect by a method for the detection of an L-nucleic acid molecule according to the first aspect, including any embodiment thereof, in a sample, wherein the method comprises the steps of a) providing a capture probe, wherein the capture probe is at least partially complementary to a first part of the L-nucleic acid molecule according to the first aspect, including any embodiment thereof, and a detection probe, wherein the detection probe is at least partially complementary to a second part of the L-nucleic acid molecule according to the first aspect, including any embodiment thereof, or, alternatively, the capture probe is at least partially complementary to a second part of the L-nucleic acid molecule according to the first aspect, including any embodiment thereof, and the detection probe is at least partially complementary to a first part of the L-nucleic acid molecule according to the first aspect, including any embodiment thereof;
b) adding the capture probe and the detection probe separately or combined to a sample containing the L-nucleic acid molecule according to the first aspect, including any embodiment thereof, or presumed to contain the L-nucleic acid molecule according to the first aspect, including any embodiment thereof;
c) allowing the capture probe and the detection probe to react either simultaneously or in any order sequentially with the L-nucleic acid molecule according to the first aspect, including any embodiment thereof;

d) optionally detecting whether or not the capture probe is hybridized to the L-nucleic acid molecule according to the first aspect, including any embodiment thereof, provided in step a); and
e) detecting the complex formed in step c) consisting of the L-nucleic acid molecule according to the first aspect, including any embodiment thereof, and the capture probe and the detection probe.

The present invention is also more specifically also solved by the following embodiments 1 to 103, whereby embodiment 1 corresponds to the first aspect, embodiment 47 corresponds to the second aspect, embodiment 49 corresponds to the third aspect, embodiment 50 corresponds to the fourth aspect, embodiment 51 corresponds to the fifth aspect, embodiment 53 corresponds to the sixth aspect, embodiment 56 corresponds to the seventh aspect, embodiment 79 corresponds to the eighth aspect, embodiment 96 corresponds to the ninth aspect, embodiment 97 corresponds to the tenth aspect, embodiment 98 corresponds to the eleventh aspect, embodiment 99 corresponds to the twelfth aspect, and embodiment 100 corresponds to the 13" aspect:

Embodiment 1: An L-nucleic acid molecule capable of binding to human CXCL8, wherein the L-nucleic acid molecule comprises a central stretch of nucleotides, wherein the central stretch of nucleotides comprises a nucleotide sequence of
5'-GGAAGUACGUGGAAAGCCRA(Xu)RAGUGU-GUCCCG-3' [SEQ. ID. NO: 27], wherein $X_U$ is U or absent.

Embodiment 2: The L-nucleic acid molecule of embodiment 1, wherein the central stretch of nucleotides comprises a nucleotide sequence selected from the group of a)
[SEQ. ID. NO: 28]
5' GGAAGUACGUGGAAAGCCAAUGAGUGUGUCCCG 3', b)
[SEQ. ID. NO: 29]
5' GGAAGUACGUGGAAAGCCGAUGAGUGUGUCCCG 3',
and c)
[SEQ. ID. NO: 30]
5' GGAAGUACGUGGAAAGCCGAAAGUGUGUCCCG 3'.

Embodiment 3: The L-nucleic acid molecule of embodiment 2, wherein the central stretch of nucleotides comprises a nucleotide sequence of

[SEQ. ID. NO: 30]
5' GGAAGUACGUGGAAAGCCGAAAGUGUGUCCCG 3'
or

[SEQ. ID. NO: 28]
5' GGAAGUACGUGGAAAGCCAAUGAGUGUGUCCCG 3',
preferably

[SEQ. ID. NO: 30]
5' GGAAGUACGUGGAAAGCCGAAAGUGUGUCCCG 3'.

Embodiment 4: The L-nucleic acid molecule of any one of embodiments 1 to 3, wherein the L-nucleic acid molecule comprises in 5'->3' direction a first terminal stretch of nucleotides, the central stretch of nucleotides and a second terminal stretch of nucleotides, wherein the first terminal stretch of nucleotides comprises three to six nucleotides, and
the second terminal stretch of nucleotides comprises three to six nucleotides, wherein preferably
the first terminal stretch of nucleotides comprises five to six nucleotides, and
the second terminal stretch of nucleotides comprises five to six nucleotides, wherein more preferably
the first terminal stretch of nucleotides comprises five nucleotides, and
the second terminal stretch of nucleotides comprises five nucleotides.

Embodiment 5: The L-nucleic acid molecule of embodiment 4, wherein the first terminal stretch of nucleotides comprises a nucleotide sequence of 5' $Z_1Z_2Z_3Z_4Z_5$C 3' and the second terminal stretch of nucleotides comprises a nucleotide sequence of 5' G$Z_6Z_7Z_8Z_9$ $Z_{10}$ 3', wherein
$Z_1$ is G or absent, $Z_2$ is S or absent, $Z_3$ is K or absent, $Z_4$ is S, $Z_5$ is D, $Z_6$ is H, $Z_7$ is S, $Z_8$ is M or absent, $Z_9$ is S or absent, and $Z_{10}$ is C or absent;
wherein preferably
a) $Z_1$ is G, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is C; or
b) $Z_1$ is absent, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is absent; or
c) $Z_1$ is absent, $Z_2$ is absent, $Z_3$ is K, $Z_4$ is S, $Z_5$ is D, $Z_6$ is H, $Z_7$ is S, $Z_8$ is M, $Z_9$ is absent, and $Z_{10}$ is absent; or
d) $Z_1$ is absent, $Z_2$ is absent, $Z_3$ is absent, $Z_4$ is S, $Z_5$ is D, $Z_6$ is H, $Z_7$ is S, $Z_8$ is absent, $Z_9$ is absent, and $Z_{10}$ is absent; or
e) $Z_1$ is absent, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is C; or
f) $Z_1$ is absent, $Z_2$ is absent, $Z_3$ is K, $Z_4$ is S, $Z_5$ is D, $Z_6$ is H, $Z_7$ is S, $Z_8$ is M, $Z_9$ is S, and $Z_{10}$ is C; or
g) $Z_1$ is absent, $Z_2$ is absent, $Z_3$ is absent, $Z_4$ is S, $Z_5$ is D, $Z_6$ is H, $Z_7$ is S, $Z_8$ is M, $Z_9$ is S, and $Z_{10}$ is C; or
h) $Z_1$ is G, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is absent; or
i) $Z_1$ is G, $Z_2$ is S, $Z_3$ is K, $Z_4$ is S, $Z_5$ is D, $Z_6$ is H, $Z_7$ is S, $Z_8$ is M, $Z_9$ is absent, and $Z_{10}$ is absent; or
j) $Z_1$ is G, $Z_2$ is S, $Z_3$ is K, $Z_4$ is S, $Z_5$ is D, $Z_6$ is H, $Z_7$ is S, $Z_8$ is absent, $Z_9$ is absent, and $Z_{10}$ is absent; or
k) $Z_1$ is absent, $Z_2$ is S, $Z_3$ is K, $Z_4$ is S, $Z_5$ is D, $Z_6$ is H, $Z_7$ is S, $Z_8$ is M, $Z_9$ is absent, and $Z_{10}$ is absent; or
l) $Z_1$ is absent, $Z_2$ is S, $Z_3$ is K, $Z_4$ is S, $Z_5$ is D, $Z_6$ is H, $Z_7$ is S, $Z_8$ is absent, $Z_9$ is absent, and $Z_{10}$ is absent; or
m) $Z_1$ is absent, $Z_2$ is absent, $Z_3$ is K, $Z_4$ is S, $Z_5$ is D, $Z_6$ is H, $Z_7$ is S, $Z_8$ is M, $Z_9$ is S, and $Z_{10}$ is absent; or
n) $Z_1$ is absent, $Z_2$ is absent, $Z_3$ is absent, $Z_4$ is S, $Z_5$ is D, $Z_6$ is H, $Z_7$ is S, $Z_8$ is M, $Z_9$ is S, and $Z_{10}$ is absent; or
o) $Z_1$ is absent, $Z_2$ is absent, $Z_3$ is K, $Z_4$ is S, $Z_5$ is D, $Z_6$ is H, $Z_7$ is S, $Z_8$ is absent, $Z_9$ is absent, and $Z_{10}$ is absent; or
p) $Z_1$ is absent, $Z_2$ is absent, $Z_3$ is absent, $Z_4$ is S, $Z_5$ is D, $Z_6$ is H, $Z_7$ is S, $Z_8$ is M, $Z_9$ is absent, and $Z_{10}$ is absent.

Embodiment 6: The L-nucleic acid molecule of any one of embodiments 4 to 5, wherein
a) the first terminal stretch of nucleotides comprises a nucleotide sequence of 5' CUGAC 3' and the second terminal stretch of nucleotides comprises a nucleotide sequence of 5' GUCAG 3';

b) the first terminal stretch of nucleotides comprises a nucleotide sequence of 5' GCUGAC 3' and the second terminal stretch of nucleotides comprises a nucleotide sequence of 5' GUCAGC 3'; or c) the first terminal stretch of nucleotides comprises a nucleotide sequence of 5' GCUGAC 3' and the second terminal stretch of nucleotides comprises a nucleotide sequence of 5' GUGAGC 3';

d) the first terminal stretch of nucleotides comprises a nucleotide sequence of 5' GUGAC 3' and the second terminal stretch of nucleotides comprises a nucleotide sequence of 5' GUCAC 3';

e) the first terminal stretch of nucleotides comprises a nucleotide sequence of 5' UGAC 3' and the second terminal stretch of nucleotides comprises a nucleotide sequence of 5' GUCA 3';

f) the first terminal stretch of nucleotides comprises a nucleotide sequence of 5' GGAC 3' and the second terminal stretch of nucleotides comprises a nucleotide sequence of 5' GUCC 3';

g) the first terminal stretch of nucleotides comprises a nucleotide sequence of 5' GCAC 3' and the second terminal stretch of nucleotides comprises a nucleotide sequence of 5' GUGC 3';

h) the first terminal stretch of nucleotides comprises a nucleotide sequence of 5' GGUC 3' and the second terminal stretch of nucleotides comprises a nucleotide sequence of 5' GACC 3';

i) the first terminal stretch of nucleotides comprises a nucleotide sequence of 5' UGGC 3' and the second terminal stretch of nucleotides comprises a nucleotide sequence of 5' GCCA 3';

j) the first terminal stretch of nucleotides comprises a nucleotide sequence of 5' GAC 3' and the second terminal stretch of nucleotides comprises a nucleotide sequence of 5' GUC 3';

wherein preferably
the first terminal stretch of nucleotides comprises a nucleotide sequence of 5' CUGAC 3' and the second terminal stretch of nucleotides comprises a nucleotide sequence of 5' GUCAG 3';
or
the first terminal stretch of nucleotides comprises a nucleotide sequence of 5' GCUGAC 3' and the second terminal stretch of nucleotides comprises a nucleotide sequence of 5' GUCAGC 3'
or
the first terminal stretch of nucleotides comprises a nucleotide sequence of 5' GUGAC 3' and the second terminal stretch of nucleotides comprises a nucleotide sequence of 5' GUCAC 3';
wherein more preferably
the first terminal stretch of nucleotides comprises a nucleotide sequence of 5' CUGAC 3' and the second terminal stretch of nucleotides comprises a nucleotide sequence of 5' GUCAG 3' or
the first terminal stretch of nucleotides comprises a nucleotide sequence of 5' GUGAC 3' and the second terminal stretch of nucleotides comprises a nucleotide sequence of 5' GUCAC 3'.

Embodiment 7: The L-nucleic acid molecule of any one of embodiments 1 to 6, wherein the L-nucleic acid molecule comprises 40 to 45 nucleotides, preferably 42 to 45 nucleotides, more preferably 42 nucleotides.

Embodiment 8: The L-nucleic acid molecule of any one of embodiments 1 to 7, wherein the L-nucleic acid molecule consists of ribonucleotides.

Embodiment 9: The L-nucleic acid molecule of any one of embodiments 1 to 8, wherein the L-nucleic acid molecule comprises a nucleotide sequence selected from the group of SEQ. ID. Nos: 14 to 26 and 39 to 44, or the L-nucleic acid molecule comprises an L-nucleic acid molecule having an identity of at least 75% to the L-nucleic acid molecule comprising a nucleotide sequence selected from the group of SEQ. ID. Nos: 14 to 26 and 39 to 44, or the L-nucleic acid molecule comprises an L-nucleic acid molecule which is homologous to the L-nucleic acid molecule comprising a nucleotide sequence selected from the group of SEQ. ID. Nos: 14 to 26 and 39 to 44, wherein the homology is at least 75%.

Embodiment 10: The L-nucleic acid molecule of embodiment 9, wherein the L-nucleic acid molecule comprises a nucleotide sequence selected from the group of SEQ. ID. NO: 16, SEQ. ID. NO: 17, SEQ. ID. NO: 25, SEQ. ID. NO: 26, SEQ. ID. NO: 39, SEQ. ID. NO: 40, SEQ. ID. NO: 20 and SEQ. ID. Nos: 41 to 44, or the L-nucleic acid molecule comprises an L-nucleic acid molecule having an identity of at least 75% to the L-nucleic acid molecule comprising a nucleotide sequence selected from the group of SEQ. ID. NO: 16, SEQ. ID. NO: 17, SEQ. ID. NO: 25, SEQ. ID. NO: 26, SEQ. ID. NO: 39, SEQ. ID. NO: 40, SEQ. ID. NO: 20 and SEQ. ID. Nos: 41 to 44, or the L-nucleic acid molecule comprises an L-nucleic acid molecule which is homologous to the L-nucleic acid molecule comprising a nucleotide sequence selected from the group of SEQ. ID. NO: 16, SEQ. ID. NO: 17, SEQ. ID. NO: 25, SEQ. ID. NO: 26, SEQ. ID. NO: 39, SEQ. ID. NO: 40, SEQ. ID. NO: 20 and SEQ. ID. Nos 41 to 44, wherein the homology is at least 75%.

Embodiment 11: The L-nucleic acid molecule of any one of embodiments 1 to 10, wherein the L-nucleic acid molecule is capable of binding to CXCL8, wherein preferably CXCL8 is human CXCL8, monkey CXCL8, rabbit CXCL8, pig CXCL8, dog CXCL8, sheep CXCL8 or guinea pig CXCL8.

Embodiment 12: The L-nucleic acid molecule of any one of embodiments 1 to 11, wherein the L-nucleic acid molecule is capable of specific binding to CXCL8, preferably human CXCL8, monkey CXCL8, rabbit CXCL8, pig CXCL8, dog CXCL8, sheep CXCL8 or guinea pig CXCL8, more preferably human CXCL8.

Embodiment 13: The L-nucleic acid molecule of any one of embodiments 1 to 12, wherein the L-nucleic acid molecule does not bind to or is incapable of binding to ELR-positive CXC chemokines different from CXCL8, wherein the ELR-positive CXC chemokines different from CXCL8 are preferably selected from the group consisting of CXCL1, CXCL2, CXCL3, CXCL5, CXCL6 and CXCL7.

Embodiment 14: The L-nucleic acid molecule of embodiment 13, wherein the L-nucleic acid molecule does not bind to or is incapable of binding to ELR-positive human CXC chemokines different from human CXCL8, wherein the ELR-positive human CXC chemokines different from human CXCL8 are preferably selected from the group consisting of human CXCL1, human CXCL2, human CXCL3, human CXCL5, human CXCL6 and human CXCL7.

Embodiment 15: The L-nucleic acid molecule of any one of embodiments 1 to 14, wherein the L-nucleic acid molecule has a binding affinity to human CXCL8, expressed as KD, of 10 nM or less, preferably of 1 nM or less, and more preferably of 100 pM or less and most preferably of 30 pM or less.

Embodiment 16: The L-nucleic acid molecule of any one of embodiments 1 to 15, wherein the L-nucleic acid molecule has a binding affinity to human CXCL8, expressed as IC50, of 10 nM or less, preferably of 1 nM or less, more preferably of 100 pM or less, and most preferably of 30 pM or less.

Embodiment 17: The L-nucleic acid molecule of any one of embodiments 1 to 16, wherein the L-nucleic acid molecule has a binding affinity to ELR-positive CXC chemokines different from CXCL8, expressed as KD, of 100 nM or more, preferably of 500 nM or more, and more preferably of 1000 nM or more.

Embodiment 18: The L-nucleic acid molecule of any one of embodiments 1 to 17, wherein the L-nucleic acid molecule has a binding affinity to ELR-positive CXC chemokines different from CXCL8, expressed as IC50, of 100 nM or more, preferably of 500 nM or more, and more preferably of 1000 nM or more.

Embodiment 19: The L-nucleic acid molecule of any one of embodiments 1 to 18, wherein the L-nucleic acid molecule has a binding affinity to human CXCL8, expressed as KD, of 10 nM or less, preferably of 1 nM or less, and more preferably of 100 pM or less, and most preferably of 30 pM or less, wherein the L-nucleic acid molecule has a binding affinity to ELR-positive CXC chemokines different from CXCL8, expressed as KD, of 100 nM or more, preferably of 500 nM or more, and more preferably of 1000 nM or more, and/or the L-nucleic acid molecule has a binding affinity to human CXCL8, expressed as IC50, of 10 nM or less, preferably of 1 nM or less, more preferably of 100 pM or less, and most preferably of 30 pM or less, wherein the L-nucleic acid molecule has a binding affinity to ELR-positive CXC chemokines different from CXCL8, expressed as IC50, of 100 nM or more, preferably of 500 nM or more, and more preferably of 1000 nM or more.

Embodiment 20: The L-nucleic acid molecule of any one of embodiments 15 to 19, wherein the binding affinity is determined at room temperature, preferably at 25° C.

Embodiment 21: The L-nucleic acid molecule of any one of embodiments 15 to 19, wherein the binding affinity is determined at 37° C.

Embodiment 22: The L-nucleic acid molecule of any one of embodiments 1 to 21, wherein the L-nucleic acid molecule is an antagonist of an activity mediated by CXCL8, preferably human CXCL8, monkey CXCL8, rabbit CXCL8, pig CXCL8, dog CXCL8, sheep CXCL8 or guinea pig CXCL8, more preferably human CXCL8.

Embodiment 23: The L-nucleic acid molecule of embodiment 22, wherein the L-nucleic acid molecule is not an antagonist of ELR-positive human CXC chemokines different from human CXCL8 or is incapable of antagonizing an activity mediated by ELR-positive CXC chemokines different from CXCL8, wherein the ELR-positive CXC chemokines different from CXCL8 are preferably selected from the group consisting of CXCL1, CXCL2, CXCL3, CXCL5, CXCL6 and CXCL7.

Embodiment 24: The L-nucleic acid molecule of embodiment 23, wherein the L-nucleic acid molecule is not an antagonist of ELR-positive human CXC chemokines different from human CXCL8 or is incapable of antagonizing an activity mediated by ELR-positive human CXC chemokines different from human CXCL8, wherein the ELR-positive human CXC chemokines different from human CXCL8 are preferably selected from the group consisting of human CXCL1, human CXCL2, human CXCL3, human CXCL5, human CXCL6 and human CXCL7.

Embodiment 25: The L-nucleic acid molecule of any one of embodiments 22 to 24, wherein the antagonistic activity of the L-nucleic acid molecule to an activity mediated by human CXCR1 and/or CXCR2, expressed as IC50, is 10 nM or less, preferably of 1 nM or less, more preferably of 100 pM or less, and most preferably of 30 pM or less.

Embodiment 26: The L-nucleic acid molecule of any one of embodiments 22 to 25, wherein the antagonistic activity of the L-nucleic acid molecule to an activity mediated by human CXCL8 is determined at 37° C.

Embodiment 27: The L-nucleic acid molecule of any one of embodiments 1 to 26, wherein the L-nucleic acid molecule comprises a modification group.

Embodiment 28: The L-nucleic acid molecule of embodiment 27, wherein the modification group is coupled to the 5'-terminal nucleotide and/or the 3'-terminal nucleotide of the L-nucleic acid molecule and/or to a nucleotide of the L-nucleic acid molecule between the 5'-terminal nucleotide of the L-nucleic acid molecule and the 3'-terminal nucleotide of the L-nucleic acid molecule.

Embodiment 29: The L-nucleic acid molecule of any one of embodiments 27 and 28, wherein the modification group is coupled to the L-nucleic acid molecule via a linker.

Embodiment 30: The L-nucleic acid molecule of embodiment 29, wherein the linker is a hydrophilic linker, preferably the hydrophilic linker comprises one or more units of ethylene glycol, more preferably the hydrophilic linker comprises triethylene glycol, hexaethylene glycol or polyethylene glycol.

Embodiment 31: The L-nucleic acid molecule of embodiment 29, wherein the linker is a biodegradable linker.

Embodiment 32: The L-nucleic acid molecule of any one of embodiments 27 to 31, wherein excretion rate of the L-nucleic acid molecule comprising the modification group from an organism is decreased compared to the excretion rate of an L-nucleic acid not comprising the modification group.

Embodiment 33: The L-nucleic acid molecule of any one of embodiments 27 to 31, wherein the L-nucleic acid molecule comprising the modification group has an increased retention time in an organism compared to the retention time in an organism of an L-nucleic acid molecule not comprising the modification group.

Embodiment 34: The L-nucleic acid molecule of any one of embodiments 32 to 33, wherein the organism is a human or an animal body, preferably a human body.

Embodiment 35: The L-nucleic acid molecule of any one of embodiments 27 and 34, wherein the modification group is selected from the group comprising a biodegradable modification and a non-biodegradable modification, preferably the modification group is selected from the group comprising polyethylene glycol, linear polyethylene glycol, branched polyethylene glycol, hydroxyethyl starch, a peptide, a protein, a polysaccharide, a sterol, polyoxypropylene, polyoxyamidate and poly(2-hydroxyethyl)-L-glutamine.

Embodiment 36: The L-nucleic acid molecule of embodiment 35, wherein the modification group is a polyethylene glycol, preferably a linear polyethylene glycol or a branched polyethylene glycol, wherein preferably the molecular weight of the polyethylene glycol is from about 20,000 to about 120,000 Da, more preferably from about 30,000 to about 80,000 Da and most preferably about 40,000 Da.

Embodiment 37: The L-nucleic acid molecule of embodiment 36, wherein the molecular weight of the polyethylene glycol is from about 20,000 to about 120,000 Da, preferably from about 30,000 to about 80,000 Da and more preferably about 40,000 Da.

Embodiment 38: The L-nucleic acid molecule of embodiment 35 wherein the modification group is hydroxyethyl starch, wherein preferably the molecular weight of the hydroxyethyl starch is from about 50 to about 1000 kDa, more preferably from about 100 to about 700 kDa and most preferably from 200 to 500 kDa.

Embodiment 39: The L-nucleic acid molecule of any one of embodiments 27 to 31, wherein the modification group is for immobilization of the L-nucleic acid molecule.

Embodiment 40: The L-nucleic acid molecule of embodiment 39, wherein the immobilization comprises covalent linkage of the L-nucleic acid molecule to a surface, wherein preferably the surface is a surface of a reaction vessel, a surface of a device in a reaction vessel or a surface of a biosensor.

Embodiment 41: The L-nucleic acid molecule of embodiment 39, wherein the immobilization comprises non-covalent linkage of the L-nucleic acid molecule to a surface, wherein preferably the surface is a surface of a reaction vessel, a surface of a device in a reaction vessel or a surface of a biosensor.

Embodiment 42: The L-nucleic acid molecule of any one of embodiments 39 to 41, wherein the modification group is selected from the group comprising carboxyl, hydroxyl, phosphatidyl, sulfonic ester, amine, thiol, epoxide, alkyne, strained cycloalkyne, maleimide, azide, hydrazide, wherein preferably strained cycloalkyne is selected from the group comprising dibenzocyclooctyl (DBCO), bicyclo[6.1.0]non-4-yne (BCN) and azadibenzocyclooctyne (ADIBO).

Embodiment 43: The L-nucleic acid molecule of embodiment 42, wherein the modification group is a strained cycloalkyne, preferably dibenzocyclooctyl (DBCO).

Embodiment 44: The L-nucleic acid molecule of embodiment 41, wherein the modification group is biotin, bromo-desoxyuridine, digoxigenin, or an oligonucleotide, preferably the modification group is biotin.

Embodiment 45: The L-nucleic acid molecule of any one of embodiments 27 to 31, wherein the modification group allows detection of the L-nucleic acid molecule, preferably the modification group is a label.

Embodiment 46: The L-nucleic acid molecule of embodiment 45, wherein the label is selected from the group comprising biotin, bromo-desoxyuridine, digoxigenin, an oligonucleotide, a fluorescent label, an electrochemoluminescence label, a radioactive label, an enzymatic label, an UV-label, colloidal gold, a nanoparticle, and a chelator molecule label.

Embodiment 47: The L-nucleic acid molecule of any one of embodiments 1 to 46, for use in a method for the treatment and/or prevention of a disease.

Embodiment 48: The L-nucleic acid molecule for use of embodiment 47, wherein the disease is associated with a CXCL8-mediated pathogenic mechanism and/or is selected from the group comprising an inflammatory disease and cancer, wherein preferably inflammatory disease is an inflammatory disease of the respiratory system, an inflammatory disease of the skin, an autoimmune disease, an inflammatory neurological disease, an ischemic disease, artherosclerosis, pancreatic islet transplant rejection, organ transplant rejection, organ delayed function, spinal cord injury or cystitis.

Embodiment 49: The L-nucleic acid molecule of any one of embodiments 1 to 47, for use in a method for detecting CXCL8.

Embodiment 50: The L-nucleic acid molecule of any one of embodiments 1 to 47, for manufacture of a detection means or a biosensor.

Embodiment 51: A pharmaceutical composition comprising an L-nucleic acid molecule as defined in any one of embodiments 1 to 50 and optionally a further constituent, wherein the further constituent is selected from the group comprising a pharmaceutically acceptable excipient, a pharmaceutically acceptable carrier and a pharmaceutically active agent.

Embodiment 52: The pharmaceutical composition of embodiment 51, wherein the pharmaceutical composition comprises an L-nucleic acid molecule as defined in any one of embodiments 1 to 50 and a pharmaceutically acceptable carrier.

Embodiment 53: Use of an L-nucleic acid molecule of any one of embodiments 1 to 50, for the manufacture of a medicament.

Embodiment 54: Use of embodiment 53, wherein the medicament is for use in human medicine or for use in veterinary medicine.

Embodiment 55: Use of embodiment 54, wherein the medicament is for the treatment and/or prevention of a disease that is associated with a CXCL8-mediated pathogenic mechanism and/or is selected from the group comprising an inflammatory disease and cancer, wherein preferably inflammatory disease is an inflammatory disease of the respiratory system, an inflammatory disease of the skin, an autoimmune disease, an inflammatory neurological disease, an ischemic disease, artherosclerosis, pancreatic islet transplant rejection, organ transplant rejection, organ delayed function, spinal cord injury or cystitis.

Embodiment 56: Use of an L-nucleic acid molecule of any one of embodiments 1 to 50, for the manufacture of a diagnostic, a diagnostic means or a biosensor.

Embodiment 57: Use of embodiment 56, wherein the diagnostic or the diagnostic means has a surface on a reaction vessel or a surface on a device in a reaction vessel.

Embodiment 58: Use of embodiment 56, wherein the biosensor has a surface.

Embodiment 59: Use of any one of embodiments 56 to 58, wherein the diagnostic, the diagnostic means or the biosensor is suitable for detecting, either directly or indirectly, CXCL8, preferably human CXCL8.

Embodiment 60: Use of any one of embodiments 56 to 57, wherein CXCL8 is detected by direct binding, in a sandwich binding assay, or in a competitive binding assay.

Embodiment 61: Use of embodiment 60, wherein direct binding comprises a detection method that only use the L-nucleic acid molecule of any one of embodiments 1 to 50 and does not use or does not involve using a second molecule different from the L-nucleic acid molecule of any one of embodiments 1 to 50 that interacts with CXCL8.

Embodiment 62: Use of embodiment 60, wherein the sandwich assay is a sandwich hybridisation assay in which the L-nucleic acid molecule of any one of embodiments 1 to 50 is immobilized to the surface and a complex of the L-nucleic acid molecule of any one of embodiments 1 to 50 and CXCL8 is detected by a detection means that binds to (an) epitope(s) of CXCL8 that are different from the one(s) bound by the L-nucleic acid molecule of any one of embodiments 1 to 50.

Embodiment 63: Use of embodiment 60, wherein the sandwich assay is a sandwich hybridisation assay in which a means that binds to (an) epitope(s) of CXCL8 that are different from the one(s) bound by L-nucleic acid molecule of any one of embodiments 1 to 50 is immobilized to the surface and the complex of such means and CXCL8 is detected by the L-nucleic acid molecule of any one of embodiments 1 to 50.

Embodiment 64: Use of embodiment 60, wherein in the competitive binding assay the L-nucleic acid molecule of any one of embodiments 1 to 50 is immobilized to a surface and the binding of the L-nucleic acid molecule of any one of embodiments 1 to 50 to CXCL8 is competed by oligonucleotide probes at least partially complementary to the L-nucleic acid molecule of any one of embodiments 1 to 50 or by CXCL8, preferably the complementarity is base complementarity more preferably based on Watson-Crick base pairing.

Embodiment 65: Use of embodiment 60, wherein in the competitive binding assay the L-nucleic acid molecule of any one of embodiments 1 to 50 is not immobilized to a surface and the binding of the L-nucleic acid molecule of any one of embodiments 1 to 50 to CXCL8 is competed by oligonucleotide probes complementary to the L-nucleic acid molecule of any one of embodiments 1 to 50 or by CXCL8, wherein preferably the oligonucleotide probes complementary to the L-nucleic acid molecule of any one of embodiments 1 to 50 or CXCL8 are immobilized to a surface, preferably the complementarity is base complementarity more preferably based on Watson-Crick base pairing.

Embodiment 66: Use of any one of embodiments 62 to 65, wherein for immobilisation to the surface the L-nucleic acid molecule of any one of embodiments 39 to 44 is used.

Embodiment 67: Use of any one of embodiments 57 to 66, wherein the surface, preferably the surface of the biosensor, is selected from the group consisting of of gold, silver, titanium, zirconium, vanadium, chromium, manganese, cobalt, tungsten, molybdenum, platinum, aluminium, iron, steel, copper, nickel, silicon, germanium, indium phosphide, gallium arsenide, and an oxide, nitride or alloy or mixture thereof, indium-tin oxide, glassy carbon, sapphire, silicate glass and borate glass.

Embodiment 68: Use of any one of embodiments 57 to 67, wherein the surface, preferably the surface of the biosensor, is modified by polylysine, an aminosilane, an epoxysilane, a nitrocellulose, a carboxydextran, a carbon nanomembrane, a graphene oxide, a carbon surface such as carbon black, a carbon fiber, a carbon plate, a carbon cloth, an activated carbon, a vitreous carbon, charcoal, an activated charcoal, a graphite powder, a graphite fiber, a carbon nanotube, a fullerene, a carboxyl group, an azide group, a thiol group, a hydroxy group, an epoxide, maleimide, an alkyne, a strained alkyne or any combination thereof.

Embodiment 69: Use of embodiment 68, wherein for immobilization of an L-nucleic acid molecule of any of embodiments 39 to 44 the surface is functionalized by a primary amine, thiol group, azide, alkyne, alkene, tetrazine, tetrazole, or strained cycloalkyne, wherein preferably strained cycloalkyne is selected from the group comprising dibenzocyclooctyl (DBCO), bicyclo[6.1.0]non-4-yne (BCN) or azadibenzocyclooctyne (ADIBO).

Embodiment 70: Use of embodiment 69, wherein for immobilization of an L-nucleic acid molecule of any of embodiments 42 to 43 the strain-promoted azide-alkyne cyloaddition is used.

Embodiment 71: Use of any one of embodiments 56 to 70, wherein the L-nucleic acid molecule of any one of embodiments 44 to 46 is used for detection.

Embodiment 72: Use of any one of embodiments 56 to 71, wherein a detection system of the biosensor is based on optical readout, mass change, refractory index, charge, surface stress and atomic force microscopy.

Embodiment 73: Use of embodiment 72, wherein the detection system of the biosensor based on optical readout is fluorescence, absorption or luminescence.

Embodiment 74: Use of embodiment 72, wherein the detection system of the biosensor based on mass change is quartz crystal microbalance or microelectromechanical systems.

Embodiment 75: Use of embodiment 72, wherein the detection system of the biosensor based on refractory index is surface plasmon resonance, a ring resonator or ellipsometry.

Embodiment 76: Use of embodiment 72, wherein the detection system of the biosensor based on charge is electrochemical impedance, voltammetry, amperometry, potentiometry, conductivity or a field effect transistor.

Embodiment 77: Use of embodiment 72, wherein the detection system of the biosensor based on surface stress is a cantilever biosensor.

Embodiment 78: Use of any one of embodiments 56 to 59, wherein CXCL8 is detected by a homogenous assay setup.

Embodiment 79: Use of an L-nucleic acid molecule of any one of embodiments 1 to 50, for the detection of CXCL8, preferably human CXCL8.

Embodiment 80: Use of embodiment 79, wherein CXCL8 is detected in a sandwich binding assay setup, a homogenous assay setup, or a competitive assay setup.

Embodiment 81: Use of embodiment 80, wherein the sandwich binding assay setup, the homogenous assay setup, or the competitive assay setup, is suitable for detecting, either directly or indirectly, CXCL8.

Embodiment 82: Use of any one of embodiments 78 to 81, wherein the L-nucleic acid molecule is covalently immobilized on a surface of a reaction vessel of a diagnostic, on a surface of a device in a reaction vessel of a diagnostic or on a surface of a biosensor.

Embodiment 83: Use of embodiment 82, wherein for immobilization the L-nucleic acid molecule of any one of embodiments 39 to 44 is used.

Embodiment 84: Use of any one of embodiments 82 to 83, wherein the surface, preferably the surface of the biosensor, is selected from the group consisting of gold, silver, titanium, zirconium, vanadium, chromium, manganese, cobalt, tungsten, molybdenum, platinum, aluminium, iron, steel, copper, nickel, silicon, germanium, indium phosphide, gallium arsenide, and an oxide, a nitride or an alloy or mixtures thereof, indium-tin oxide, glassy carbon, sapphire, a silicate glass and a borate glass.

Embodiment 85: Use of any one of embodiments 82 to 84, wherein the surface, preferably the surface of the biosensor, is modified by polylysine, an aminosilane, an epoxysilane, a nitrocellulose, a carboxydextran, a carbon nanomembrane, graphene oxide, a carbon surface such as carbon black, carbon fiber, a carbon plate, a carbon cloth, an activated carbon, a vitreous carbon, a charcoal, an activated charcoal, a graphite powder, a graphite fiber, a carbon nanotube, a fullerene, a carboxyl group, an azide group, a thiol group, a hydroxy group, an epoxide, maleimide, an alkyne, a strained alkyne or any combination thereof.

Embodiment 86: Use of embodiment 85, wherein for immobilization of an L-nucleic acid molecule of any of embodiments 38 to 44 the surface is functionalized by an activated activated primary amine, thiol group, azide or strained cycloalkyne, wherein preferably strained cycloalkyne is selected from the group comprising dibenzocyclooctyl (DBCO), bicyclo[6.1.0]non-4-yne (BCN) or azadibenzocyclooctyne (ADIBO).

Embodiment 87: Use of embodiment 86, wherein for immobilization of an L-nucleic acid molecule of any one of embodiments 42 to 43 the strain-promoted azide-alkyne cyloaddition is used.

Embodiment 88: Use of any one of embodiments 82 to 87, wherein a detection system of the biosensor is based on optical readout, mass change, refractory index, charge, surface stress and atomic force microscopy.

Embodiment 89: Use of embodiment 88, wherein the detection system of the biosensor based on optical readout is fluorescence, absorption or luminescence.

Embodiment 90: Use of embodiment 85, wherein the detection system of the biosensor based on mass change is quartz crystal microbalance system or a microelectromechanical system.

Embodiment 91: Use of embodiment 88, wherein the detection system of the biosensor based on refractory index is surface plasmon resonance, a ring resonator or ellipsometry.

Embodiment 92: Use of embodiment 88, wherein the detection system of the biosensor based on charge is electrochemical impedance, voltammetry, amperometry, potentiometry, conductivity or a field effect transistor.

Embodiment 93: Use of embodiment 88, wherein the detection system of the biosensor based on surface stress is a cantilever biosensor.

Embodiment 94: Use of any one of embodiments 79 to 81, wherein the L-nucleic acid molecule comprises a modification group that allows detection of the L-nucleic acid molecule, preferably the modification group is a label.

Embodiment 95: Use of embodiment 94, wherein the label is selected from the group comprising biotin, bromo-desoxyuridine, digoxigenin, an oligonucleotide, a fluorescent label, an electrochemoluminescence label, a radioactive label, an enzymatic label, an UV-label, colloidal gold, a nanoparticle, and a chelator molecule label.

Embodiment 96: A kit for the detection of CXCL8, wherein the kit comprises an L-nucleic acid molecule of any one of embodiments 1 to 50 and at least an instruction leaflet or a reaction vessel.

Embodiment 97: A method for the detection of CXCL8 using the L-nucleic acid as defined in any one of embodiments 1 to 50 in a sample, wherein the method comprises the steps of.
 a) providing a sample with unknown concentration of CXCL8;
 b) bringing the sample or a dilution thereof in contact with a diagnostic, diagnostic means or biosensor as defined in any one of the embodiments 56-78;
 c) measuring the signal with a diagnostic, diagnostic means or biosensor as defined in any one of the embodiments 56-78;
 d) optionally, comparing the signal with a reference;
 e) optionally, the concentration of CXCL8 in a sample with unknown CXCL8 concentration is determined by comparison with signals obtained from at least one sample with known CXCL8 concentration, preferably the at least one sample with a known CXCL8 concentration is subject to steps b) to c).

Embodiment 98: A complex comprising an L-nucleic acid molecule of any one of embodiments 1 to 50 and CXCL8, wherein preferably the complex is a crystalline complex.

Embodiment 99: A method for the screening of an antagonist of an activity mediated by CXCL8 comprising the following steps:
 providing a candidate antagonist of the activity mediated by CXCL8,
 providing an L-nucleic acid molecule as defined in any one of embodiments 1 to 50,
 providing a test system which provides a signal in the presence of an antagonist of the activity mediated by CXCL8, and
 determining whether the candidate antagonist of the activity mediated by CXCL8 is an antagonist of the activity mediated by CXCL8.

Embodiment 100: A method for the detection of an L-nucleic acid as defined in any one of embodiments 1 to 50 in a sample, wherein the method comprises the steps of
 a) providing a capture probe, wherein the capture probe is at least partially complementary to a first part of the L-nucleic acid molecule as defined in any one of embodiments 1 to 50 and a detection probe, wherein the detection probe is at least partially complementary to a second part of the L-nucleic acid molecule as defined in any one of embodiments 1 to 50, or, alternatively, the capture probe is at least partially complementary to a second part of the L-nucleic acid molecule as defined in any one of embodiments 1 to 50 and the detection probe is at least partially complementary to a first part of the L-nucleic acid molecule as defined in any one of embodiments 1 to 50;
 b) adding the capture probe and the detection probe separately or combined to a sample containing the L-nucleic acid molecule as defined in any one of embodiments 1 to 50 or presumed to contain the L-nucleic acid molecule as defined in any one of embodiments 1 to 50;
 c) allowing the capture probe and the detection probe to react either simultaneously or in any order sequentially with the L-nucleic acid molecule as defined in any one of embodiments 1 to 50 or part thereof;

d) optionally detecting whether or not the capture probe is hybridized to the L-nucleic acid molecule as defined any one of embodiments 1 to 50 provided in step a); and e) detecting the complex formed in step c) consisting of the L-nucleic acid molecule as defined in any one of embodiments 1 to 50 and the capture probe and the detection probe.

Embodiment 101: The method of embodiment 100, wherein the detection probe comprises a detection means, and/or wherein the capture probe is immobilized to a support, preferably a solid support.

Embodiment 102: The method of embodiment 100 or 101, wherein any detection probe which is not part of the complex formed in step c) is removed from the reaction so that in step e) only a detection probe which is part of the complex, is detected.

Embodiment 103: The method of any one of embodiments 100 to 102, wherein step e) comprises the step of comparing the signal generated by the detection means when the capture probe and the detection probe are hybridized in the presence of the L-nucleic acid molecule as defined in any one of embodiments 1 to 50 or part thereof, and in the absence of said L-nucleic acid molecule as defined in any one of embodiments 1 to 50.

While not wishing to be bound by any theory, the present inventors have surprising found that the biostable L-nucleic acid molecule according to the present invention binds specifically and with high affinity to human CXCL8, thereby effectively inhibiting the binding of CXCL8 to its receptors. Surprisingly, the inventors identified a nucleic acid molecule that specifically bind and inhibits CXCL8 but does not bind and inhibit, respectively, related chemokines CXCL1, CXCL2, CXCL3, CXCL5, CXCL6 and CXCL7 although these proteins share structural features with CXCL8 like the ELR motif. The shown affinity in the picomolar range and the high selectivity of the CXCL8 binding nucleic could not be foreseen.

In particular, the instant inventors have surprisingly found that the nucleic acid molecule according to the present invention is suitable to block the interaction of CXCL8 with its receptors and inhibits CXCL8-induced chemotaxis with an inhibitory constant in the picomolar range. Insofar, the nucleic acid molecule according to the present invention can also be viewed as an antagonist of the effects of CXCL8, in particular the effects of CXCL8 on its receptors CXCR1 and/or CXCR2. As preferably used in herein, an antagonist to CXCL8 is a molecule that binds to CXCL8—such as the nucleic acid molecules according to the present invention—and inhibits the function of CXCL8, preferably in an in vitro assay as described in the Examples or in an in vivo model.

It is within the present invention that the nucleic acid molecule according to the present invention is a nucleic acid. Insofar the terms nucleic acid and nucleic acid molecule are used herein in a synonymous manner if not indicated to the contrary. Moreover, such nucleic acid(s) is/are preferably also referred to herein as the nucleic acid molecule(s) according to the (present) invention, the nucleic acid(s) according to the present invention, the inventive nucleic acid(s) or the inventive nucleic acid molecule(s).

The features of the nucleic acids according to the present invention as described herein can be realised in any aspect of the present invention, including any embodiment thereof, where the nucleic acid is used, either alone or in any combination. It is to be acknowledged that any embodiment of an aspect of the present invention is als an embodiment of each and any other aspect of the present invention. More specifically, any embodiment of the first aspect of the present invention is also an embodiment of each and any of the second, third, fourth, fifth, sixth, seventh, eighth, ninth, tenth, eleventh, twelfth and 13$^{th}$ aspect.

As to the various diseases, conditions and disorders which may be treated or prevented by using the nucleic acid molecule according to the present invention and compositions, preferably pharmaceutical compositions comprising the same, it has to be acknowledged that such diseases, conditions and disorders are preferably those which are described herein, including and in particular those described and set forth in the introductory part of the instant application. Insofar, the respective passages of the specification and the introductory part of the specification form an integral part of the present disclosure teaching the suitability of the nucleic acid molecule of the present invention for the prevention and treatment, respectively, for said diseases, conditions, and disorders. Additionally, a nucleic acid molecule according to the present invention is preferred if the physiological effect of the CXCL8—CXCR1 receptor and CXCL8-CXCR2 receptor axis is related to higher plasma levels of CXCL8.

As preferably used herein the term CXCL8 refers to any CXCL8 including, but not limited to, mammalian CXCL8. Preferably, the mammalian CXCL8 is selected from the group comprising human, monkey, rabbit, pig, dog, sheep, zebrafish, and guinea pig CXCL8. More preferably the CXCL8 is human CXCL8, preferably having the amino acid sequence according to SEQ ID No 2.

As outlined in more detail in the claims and example 1, the present inventors could surprisingly identify a number of different nucleic acid molecules capable of binding human CXCL8.

As outlined in more detail herein, the present inventors have identified a number of different CXCL8 nucleic acid molecules capable of binding human CXCL8, whereby the nucleic acid molecules can be characterised in terms of stretches of nucleotides which are also referred to herein as disclosed (see Example 1).

Each of the different types of CXCL8 binding nucleic acid molecule of the invention that bind to CXCL8 comprises three different stretches of nucleotides: a first terminal stretch of nucleotides, a central stretch of nucleotides and a second terminal stretch of nucleotides. In general, a CXCL8 binding nucleic acid molecule of the present invention comprise at its 5'-end and the 3'-end each a the terminal stretches of nucleotides, i.e. the first terminal stretch of nucleotides, and/or a second terminal stretch of nucleotides (also referred to as 5'-terminal stretch of nucleotides and 3'-terminal stretch of nucleotides, respectively). The first terminal stretch of nucleotides and the second terminal stretch of nucleotides can, in principle due to their base complementarity, hybridize to each other, whereby upon hybridization a double-stranded structure is formed. However, such hybridization is not necessarily realized in the molecule under physiological and/or non-physiological conditions. The three stretches of nucleotides of CXCL8 binding nucleic acid molecules —the first terminal stretch of nucleotides, the central stretch of nucleotides and second terminal stretch of nucleotides —are arranged to each other in 5'→3'-direction: the first terminal stretch of nucleotides —the central stretch of nucleotides —the second terminal stretch of nucleotides. Alternatively, the second terminal stretch of nucleotides, the central stretch of nucleotides and the first terminal stretch of nucleotides are arranged to each other in 5'→3'-direction.

The length of the central stretch of nucleotides of the nucleic acids according to the present invention is preferably 32 or 33 nucleotides.

The length of the first terminal stretch of nucleotides of the nucleic acids according to the present invention is between three and six nucleotides, preferably between five and six nucleotides, more preferably five nucleotides.

The length of the second terminal stretch of nucleotides of the nucleic according to the present invention is between three and six nucleotides, preferably between five and six nucleotides, more preferably five nucleotides.

The terms 'stretch' and 'stretch of nucleotides' are used herein in a synonymous manner if not indicated to the contrary.

The differences in the sequences of the defined stretches between the different CXCL8 binding nucleic acid molecules may influence the binding affinity to CXCL8. Based on binding analysis of the different CXCL8 binding nucleic acid molecules of the present invention the central stretch and the nucleotides forming the same are individually and more preferably in their entirety essential for binding of the CXCL8 binding nucleic acid molecule to CXCL8.

In a preferred embodiment the nucleic acid molecule according to the present invention is a single nucleic acid molecule. In a further embodiment, the single nucleic acid molecule is present as a multitude of the single nucleic acid molecule or as a multitude of the single nucleic acid molecule species.

It will be acknowledged by the ones skilled in the art that the nucleic acid molecule in accordance with the invention preferably consists of nucleotides which are covalently linked to each other, preferably through phosphodiester links or linkages.

It is within the present invention that the nucleic acid molecule according to the present invention comprises two or more stretches or part(s) thereof that can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of hybridisation, such hybridisation does not necessarily occur over the entire length of the two stretches where, at least based on the rules for base pairing, such hybridisation and thus formation of a double-stranded structure may, in principle, occur. As preferably used herein, a double-stranded structure is a part of a nucleic acid molecule or a structure formed by two or more separate strands or two spatially separated stretches of a single strand of a nucleic acid molecule, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or may form such double-stranded structure. It is also to be acknowledged that the feature that two stretches hybridize preferably indicates that such hybridization is assumed to happen due to base complementarity of the two stretches regardless of whether such hybridization actually occurs in vivo and/or in vitro. In connection with the present invention such stretches are the first terminal stretch of nucleotides and the second terminal stretch of nucleotides which, in an embodiment, may hybridize as defined above.

In a preferred embodiment the term arrangement as used herein, means the order or sequence of structural or functional features or elements described herein in connection with the nucleic acids molecule(s) disclosed herein.

The nucleic acid molecule according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%. The actual percentage of homologous nucleotides present in the nucleic acid molecule according to the present invention will depend on the total number of nucleotides present in the nucleic acid molecule. The percent modification can be based upon the total number of nucleotides present in the nucleic acid molecule.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the reference sequence. In an embodiment, the reference sequence is a nucleic acid molecule as described herein, preferably a nucleic acid molecule having a sequence according to any one of SEQ. ID. Nos: 14 to 26 and 39 to 44, preferably SEQ. ID. NO: 16, SEQ. ID. NO: 17, SEQ. ID. NO: 25, and SEQ. ID. NO: 26, SEQ. ID. NO: 39, SEQ. ID. NO: 40, SEQ. ID. NO: 20 and SEQ. ID. Nos: 41 to 44. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BEST-FIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g.

Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al., 2004).

The nucleic acid molecule according to the present invention shall also comprise a nucleic acid molecule which has a certain degree of identity relative to the nucleic acids disclosed and described herein and defined by their nucleotide sequence. More preferably, the instant invention also comprises a nucleic acid molecule which has an identity of at least 75%, preferably 85%, more preferably 90% and most preferably more than 95%, 96%, 97%, 98% or 99% relative to a nucleic acid molecule disclosed and described herein and defined by its nucleotide sequence or a part thereof.

The term inventive nucleic acid or nucleic acid molecule according to the present invention shall also comprise a nucleic acid molecule comprising the nucleic acids sequences disclosed or described herein or part thereof, preferably to the extent that the nucleic acid molecule or said parts are involved in the binding to human CXCL8. Such nucleic acid is, in an embodiment, one of the nucleic acid molecules described or disclosed herein, or a derivative and/or a metabolite thereof, whereby such derivative and/or metabolite are preferably a truncated nucleic acid molecule compared to the nucleic acid molecules described or disclosed herein.

Truncation may be related to either or both of the ends of the nucleic acid molecules as disclosed or described herein. Also, truncation may be related to the inner sequence of nucleotides of the nucleic acid molecule, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the nucleic acid(s) described or disclosed herein, whereby the stretch can be as little as one nucleotide long. The binding of a nucleic acid molecule according to the present invention can be determined by the ones skilled in the art using routine experiments or by using or adopting a method as described herein, preferably as described herein in the example part.

The nucleic acid molecule according to the present invention may be either a D-nucleic acid molecule or an L-nucleic acid molecule. Preferably, the nucleic acid molecule according to the present invention is an L-nucleic acid molecule.

It is also within the present invention that, in an embodiment, each and any of the nucleic acid molecules described herein in their entirety in terms of their nucleic acid sequence(s) are limited to the particular indicated nucleotide sequence(s). In other words, the terms "comprising" or "comprise(s)" shall be interpreted in such embodiment in the meaning of containing or consisting of.

It is also within the present invention that the nucleic acid molecule according to the present invention is part of a longer nucleic acid molecule whereby this longer nucleic acid comprises several parts whereby at least one such part is a nucleic acid according to the present invention, or a part thereof. The other part(s) of such longer nucleic acid molecule can be either one or several D-nucleic acid molecule(s) or one or several L-nucleic acid moelcule(s). Any combination may be used in connection with the present invention. These other part(s) of the longer nucleic acid molecule either alone or taken together, either in their entirety or in a particular combination, can exhibit a function which is different from binding, preferably from binding to CXCL8. One possible function is to allow interaction with other molecules, whereby such other molecules preferably are different from CXCL8, such as, e.g., for immobilization, cross-linking, detection or amplification. In a further embodiment of the present invention the nucleic acid molecule according to the invention comprises, as individual or combined moieties, several of the nucleic acid molecules of the present invention. Such nucleic acid molecule comprising several of the nucleic acids of the present invention is also encompassed by the term longer nucleic acid.

An L-nucleic acid as used herein is a nucleic acid or nucleic acid molecule consisting of L-nucleotides, preferably consisting completely of L-nucleotides.

A D-nucleic acid as used herein is nucleic acid or nucleic acid molecule consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'->3' direction.

As preferably used herein any position of a nucleotide is determined or referred to relative to the 5' end of a sequence, a stretch or a substretch containing such nucleotide. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

The nucleic acid molecule according to the present invention consists of ribonucleotides, wherein G is guanosine-5'-monophosphate, C is cytidine 5'-monophosphate, A is adenosine-5'-monophosphate, U is uridine-5' monophosphate.

For definition of ribonucleotide sequence motifs, the IUPAC abbreviations for ambiguous nucleotides are used:

| | | |
|---|---|---|
| S | strong | G or C; |
| W | weak | A or U (T); |
| R | purine | G or A; |
| Y | pyrimidine | C or U (T); |
| K | keto | G or U (T); |
| M | imino | A or C; |
| B | not A | C or U (T) or G; |
| D | not C | A or G or U(T); |
| H | not G | A or C or U (T); |
| V | not U | A or C or G; |
| N | all | A or G or C or U (T) |

Designing the nucleic acid molecule of the invention as an L-nucleic acid molecule is advantageous for several reasons. L-nucleic acid molecules are enantiomers of naturally occurring nucleic acid molecules. D-nucleic acid molecules, however, are not very stable in aqueous solutions and particularly in biological systems or biological samples due to the widespread presence of nucleases. Naturally occurring nucleases, particularly nucleases from animal cells are not capable of degrading L-nucleic acids. Because of this, the biological half-life of an L-nucleic acid molecule is significantly increased in such a system, including the animal and human body. Due to the lacking degradability of L-nucleic acid molecules no nuclease degradation products are generated and thus no side effects arising therefrom observed in such a system including the animal and human body. This aspect distinguishes L-nucleic acid molecules from factually all other compounds which are used in the therapy of diseases and/or disorders involving the presence of CXCL8. An L-nucleic acid molecule which specifically binds to a target molecule through a mechanism different from Watson Crick base pairing, or an aptamer which consists partially or completely of L-nucleotides, particularly with those parts of the aptamer being involved in the binding of the aptamer to the target molecule, is also called a spiegelmer. Aptamers and spiegelmers as such are known to a person skilled in the art and are, among others, described in 'The Aptamer Handbook' (eds. Klussmann, 2006).

It is also within the present invention that the nucleic acid molecule of the invention, regardless whether it is present as a D-nucleic acid molecule, L-nucleic acid molecule or D, L-nucleic acid molecule, may be present as single stranded or double stranded nucleic acid molecule. Typically, the nucleic acid molecule is a single stranded nucleic acid molecule which exhibits a defined secondary structure due to its primary sequence and may thus also form a tertiary structure. The nucleic acid molecule, however, may also be double stranded in the meaning that two strands which are complementary or partially complementary to each other are hybridised to each other.

The nucleic acid molecule of the invention may be modified. Such modification may be related to the single nucleotide of the nucleic acid molecule and is well known in the art. Examples for such modification are described by, among others, Venkatesan et al. (Venkatesan et al., 2003) and Kusser (Kusser, 2000). Such modification can be a H atom, a F atom or O—CH$_3$ group or NH2-group at the 2' position of one, several of all of the individual nucleotides of which the nucleic acid molecule consists. Also, the nucleic acid molecule according to the present invention can comprise at least one LNA nucleotide. In an embodiment the nucleic acid molecule according to the present invention consists of LNA nucleotides.

In an embodiment, the nucleic acid molecule according to the present invention may be a multipartite nucleic acid molecule. A multipartite nucleic acid molecule as used herein is a nucleic acid molecule which consists of at least two separate nucleic acid strands. These at least two nucleic acid strands form a functional unit whereby the functional unit is a ligand to a target molecule and, preferably an antagonist to the target molecule, in the instant case of CXCL8.

The at least two nucleic acid strands may be derived from any of the nucleic acid molecule of the invention by either cleaving a nucleic acid molecule of the invention to generate at least two strands or by synthesising one nucleic acid molecule corresponding to a first part of the full-length nucleic acid molecule of the invention and another nucleic acid molecule corresponding to another part of the full-length nucleic acid molecule of the invention. Depending on the number of parts forming the full-length nucleic acid molecules the corresponding number of parts having the required nucleotide sequence will be synthesized. It is to be acknowledged that both the cleavage approach and the synthesis approach may be applied to generate a multipartite nucleic acid molecule where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally, it is also within the present invention that a fully closed, i.e. circular structure for the nucleic acid molecule according to the present invention is realized, i.e. that the nucleic acid molecule according to the present invention are closed in an embodiment, preferably through a covalent linkage, whereby more preferably such covalent linkage is made between the 5' end and the 3' end of the nucleic acid sequence of the nucleic acid molecule of the invention as disclosed herein or any derivative thereof.

A possibility to determine the binding constants of a nucleic acid molecule according to the present invention is the use of the methods as described in example 3 and 4 which confirms the above finding that the nucleic acid molecule according to the present invention exhibits a favourable $K_D$ value range. An appropriate measure in order to express the intensity of the binding between the individual nucleic acid molecule and the target which is in the present case CXCL8 is the so-called $K_D$ value which as such as well the method for its determination are known to the one skilled in the art.

Preferably, the $K_D$ value shown by the nucleic acids according to the present invention is below 1 μM. A $K_D$ value of about 1 μM is said to be characteristic for a non-specific binding of a nucleic acid to a target. As will be acknowledged by the ones skilled in the art, the $K_D$ value of a group of compounds such as the nucleic acid molecule according to the present invention is within a certain range. The above-mentioned $K_D$ of about 1 μM is a preferred upper limit for the $K_D$ value. The lower limit for the $K_D$ of target binding nucleic acids can be as little as about 10 picomolar or can be higher. It is within the present invention that the $K_D$ values of individual nucleic acids binding to CXCL8 is preferably within this range. Preferred ranges can be defined by choosing any first number within this range and any second number within this range. Preferred upper $K_D$ values are 250 nM, 100 nM and 20 nM, preferred lower $K_D$ values are 10 nM or below, 1 nM or below, 100 μM or below and 30 μM or below. The more preferred upper $K_D$ value is 20 nM, the more preferred lower $K_D$ value is 30 μM or below.

In addition to the binding properties of the nucleic acid molecule according to the present invention, the nucleic acid molecule according to the present invention inhibits the function of the respective target molecule which is in the present case CXCL8. The inhibition of the function of CXCL8—for instance the stimulation of the respective receptors as described previously—is achieved by a binding of nucleic acid molecule according to the present invention to CXCL8 and forming a complex of a nucleic acid molecule according to the present invention and CXCL8. Such complex of a nucleic acid molecule and CXCL8 cannot stimulate the receptors that normally are stimulated by CXCL8, i.e. CXCL8 which is not present in a complex with a nucleic acid molecule of the invention. Accordingly, the inhibition of receptor function by a nucleic acid molecule according to the present invention is independent from the respective receptor that can be stimulated by CXCL8 but results from preventing the stimulation of the receptor by CXCL8 by a nucleic acid molecule according to the present invention.

A possibility to determine the inhibitory constant of the nucleic acid molecule according to the present invention is the use of the methods as described in example 5 which confirms the above finding that the nucleic acid molecule according to the present invention exhibit a favourable inhibitory constant which allows the use of said nucleic acids in a therapeutic treatment scheme.

An appropriate measure in order to express the intensity of the inhibitory effect of the individual nucleic acid molecule on interaction of the target which is in the present case CXCL8 and the respective receptor, is the so-called half maximal inhibitory concentration (abbr. $IC_{50}$) which as such as well the method for its determination are known to the one skilled in the art.

Preferably, the $IC_{50}$ value shown by a nucleic acid molecule according to the present invention is below 1 μM. An $IC_{50}$ value of about 1 μM is said to be characteristic for a non-specific inhibition of target functions by a nucleic acid molecule. As will be acknowledged by the ones skilled in the art, the $IC_{50}$ value of a group of compounds such as the nucleic acid molecules according to the present invention is within a certain range. The above-mentioned $IC_{50}$ of about 1 μM is a preferred upper limit for the $IC_{50}$ value. The lower limit for the $IC_{50}$ of a target binding nucleic acid molecule can be as little as about 10 picomolar or can be higher. It is within the present invention that the $IC_{50}$ values of individual nucleic acids binding to CXCL8 is preferably within this range. Preferred ranges can be defined by choosing any first number within this range and any second number within this range. Preferred upper $IC_{50}$ values are 250 nM and 100 nM and 20 nM, preferred lower $IC_{50}$ values are 10 nM or below, 1 nM or below, 500 μM or below and 260 μM or below. The more preferred upper $IC_{50}$ value is 20 nM, the more preferred lower $IC_{50}$ value is 260 µM or below.

The nucleic acid molecule according to the present invention may have any length provided that they are still able to bind to the target molecule. It will be acknowledged in the art that there are preferred lengths of the nucleic acid molecule according to the present inventions.

Typically, the length is between 15 and 120 nucleotides. It will be acknowledged by the ones skilled in the art that any integer between 15 and 120 is a possible length for the nucleic acid molecule according to the present invention. More preferred ranges for the length of the nucleic acid molecule according to the present invention are lengths of about 20 to 100 nucleotides, about 20 to 80 nucleotides, about 20 to 60 nucleotides, about 38 to 45 nucleotides and about 40 to 45 nucleotides.

It is within the present invention that a nucleic acid molecule of the present invention comprises a moiety which preferably is a high molecular weight moiety and/or which preferably allows to modify the characteristics of the nucleic acid molecule in terms of, among others, residence time in the animal body, preferably the human body. A particularly preferred embodiment of such modification is PEGylation and HESylation of a nucleic acid molecule according to the present invention. As used herein PEG stands for poly (ethylene glycole) and HES for hydroxyethly starch. PEGylation as preferably used herein is the modification of a nucleic acid molecule according to the present invention whereby such modification consists of a PEG moiety which is attached to a nucleic acid molecule according to the present invention. HESylation as preferably used herein is the modification of a nucleic acid molecule according to the present invention whereby such modification consists of a HES moiety which is attached to a nucleic acid molecule according to the present invention. These modifications as well as the process of modifying a nucleic acid molecule using such modifications, is described in patent applications EP 1 306 382 and WO2018099600A1, the disclosure of which is herewith incorporated in its entirety by reference.

In the case of PEG being such high molecular weight moiety, the molecular weight is preferably about 20,000 to about 120,000 Da, more preferably from about 30,000 to about 80,000 Da and most preferably about 40,000 Da. In another preferred embodiment, the PEG is a PEG as described in the international patent application WO03076490. In the case of HES being such high molecular weight moiety the molecular weight is preferably from about 50 kDa to about 1000 kDa, more preferably from about 100 kDa to about 700 kDa and most preferably from 200 kDa to 500 kDa. HES exhibits a molar substitution of 0.1 to 1.5, more preferably of 1 to 1.5 and exhibits a substitution grade expressed as the C2/C6 ratio of approximately 0.1 to 15, preferably of approximately 3 to 10. The process of HES modification is, e.g., described in German patent application DE 1 2004 006 249.8 the disclosure of which is herewith incorporated in its entirety by reference.

The modification can, in principle, be made to the nucleic acid molecule of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or indirectly, preferably indirectly through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in international patent applications WO2005/074993 and WO2003/035665.

In a preferred embodiment the linker is a biodegradable linker. The biodegradable linker allows to modify the characteristics of the nucleic acid molecule according to the present invention in terms of, among other, residence time in an animal body, preferably in a human body, due to release of the modification from the nucleic acid molecule according to the present invention.

Usage of a biodegradable linker may allow a better control of the residence time of the nucleic acid molecule according to the present invention. A preferred embodiment of such biodegradable linker is a biodegradable linker as described in, but not limited to, international patent applications WO2006/052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows modifying the characteristics of the nucleic acid molecule according to the present invention in terms of, among other, residence time in an animal body, preferably in a human body, due to release or degradation of the modification from the nucleic acid molecule according to the present invention. Usage of a biodegradable modification may allow a better control of the residence time of the nucleic acid molecule according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

In a further preferred embodiment, the linker is of the following structure:

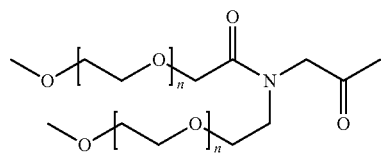

A respective linker is, for example disclosed in WO 2015/062743. As evident from the above structure the linker links two separate PEG moieties to a OH group of a phosphate moiety of a nucleotide for the nucleic acid molecule according to the invention.

Beside the modifications as described above, other modifications can be used to modify the characteristics of the nucleic acid molecule according to the present invention, whereby such other modifications may be selected from the group of proteins, lipids such as cholesterol and sugar chains such as amylase, dextran etc.

Without wishing to be bound by any theory, by modifying the nucleic acid molecule according to the present invention with a high molecular weight moiety such as a polymer and more particularly one or several of the polymers disclosed herein, which are preferably physiologically acceptable, the excretion kinetic of the thus modified nucleic acid molecule of the invention from an animal or human body to which the modified nucleic acid molecule of the invention is administered is changed. More particularly, due to the increased molecular weight of the modified nucleic acid molecule of the invention and due to the nucleic acid molecule of the invention not being subject to metabolism particularly when in the L form, i.e. being an L-nucleic acid molecule, excretion from an animal body, preferably from a mammalian body and more preferably from a human body is decreased. As excretion typically occurs via the kidneys, the present inventors assume that the glomerular filtration rate of the thus modified nucleic acid molecule is significantly reduced compared to a nucleic acid molecule not having this kind of high molecular weight modification which results in an increase in the residence time of the modified nucleic acid molecule in the animal body. In connection therewith, it is particularly noteworthy that, despite such high molecular weight modification the specificity of the nucleic acid molecule according to the present invention is not affected in a detrimental manner. Insofar, the nucleic acid molecule according to the present invention has among others, the surprising characteristic —which normally cannot be expected from a pharmaceutically active compound —that a pharmaceutical formulation providing for a sustained release is not necessarily required for providing a sustained release of the nucleic acid molecule according to the present invention. Rather, the nucleic acid molecule according to the present invention in its modified form comprising a high molecular weight moiety, can as such already be used as a sustained release-formulation as it acts, due to its modification, already as if it was released from a sustained-release formulation. Insofar, the modification(s) of the nucleic acid molecule according to the present invention as disclosed herein and the thus modified nucleic acid molecule according to the present invention and any composition comprising the same may provide for a distinct, preferably controlled pharmacokinetics and biodistribution thereof. This also includes residence time in the circulation of the animal and human body and distribution to tissues in such animal and human. Such modifications are further described in the patent application WO2003/035665.

However, it is also within the present invention that the nucleic acid molecule according to the present invention does not comprise any modification and particularly no high molecular weight modification such as PEG or HES. Such embodiment is particularly preferred when the nucleic acid molecule according to the present invention shows preferential distribution to any target organ or tissue in the body or when a fast clearance of the nucleic acid molecule according to the present invention from the body after administration is desired. A nucleic acid molecule according to the present invention as disclosed herein with a preferential distribution profile to any target organ or tissue in the body allows establishment of effective local concentrations in the target tissue while keeping systemic concentration of the nucleic acid molecule low. This allows the use of low doses which is not only beneficial from an economic point of view, but also reduces unnecessary exposure of other tissues to the nucleic acid molecule, thus reducing the potential risk of side effects. Fast clearance of the nucleic acid molecule according to the present invention from the body after administration might be desired, among others, in case of in vivo imaging or specific therapeutic dosing requirements using the nucleic acid molecule according to the present invention or medicaments comprising the same.

The inventive nucleic acid, which are also referred to herein as the nucleic acid according to the present invention or the nucleic acid molecule accordant to the (present) invention, and/or the antagonists according to the present invention may be used for the generation or manufacture of a medicament. Such medicament or a pharmaceutical composition according to the present invention contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and the nucleic acid molecule according to the invention for use in the treatment and/ore prevention and/or diagnosis of any disease as disclosed or described herein, and vice versa.

The indication, diseases and disorders for the treatment and/or prevention of which the nucleic acids, the pharmaceutical compositions and medicaments in accordance with or prepared in accordance with the present invention result from the involvement, either direct or indirect, of CXCL8 in the respective pathogenetic mechanism.

CXCL8 (UniProtKB/Swiss-Prot P10145, IL8_HUMAN; SEQ ID NO: 2), also known as interleukin 8 (IL-8), neutrophil-activating protein 1 (NAP-1), monocyte-derived neutrophil chemotactic factor (MDNCF), or granulocyte chemotactic protein 1 (GCP-1), is a small basic protein that belongs to a subfamily of CXC chemokines with pro-inflammatory and pro-angiogenic properties characterized by a glutamate-leucine-arginine (ELR) motif at the N-terminus. ELR-positive chemokines CXCL1 (also known as growth-regulated alpha protein, Gro-alpha, Melanoma growth stimulatory activity, MGSA, or NAP-3), CXCL2 (also known as Gro-beta or Macrophage inflammatory protein 2-alpha, MIP2-alpha), CXCL3 (also known as Gro-gamma or MIP2-beta), CXCL5 (also known as epithelial-derived neutrophil-activating protein 78, ENA-78, or small-inducible cytokine B5), CXCL6 (also known as chemokine alpha 3, CKA-3, granulocyte chemotactic protein 2, GCP-2, or small-inducible cytokine B6), CXCL7 (also known as platelet basic protein, PBP, leukocyte-derived growth factor, LDGF, macrophage-derived growth factor, MDGF, or small-inducible cytokine B7), and CXCL8 are agonists of the receptor CXCR2 (also known as IL8RB, IL8R type 2, CD182, CDw128b, or GRO/MGSA receptor). CXCL6, CXCL7, and CXCL8 are agonists of the receptor CXCR1 (also known as IL8RA, IL8R type 1, CD181, or CDw128a). CXCL8 binds to receptors CXCR1 and CXCR2 with similar affinities of circa 4 nM. CXCL8 binding to CXCR1/2 triggers Gui-dependent signaling pathways and, for example, induces neutrophil migration, degranulation and oxidative burst. Receptor sensitivity can be regulated by phosphorylation, beta-arrestin recruitment and receptor internalization (Ha, Theranostics 2017). CXCL7 has the highest homology to CXCL8 with 33 identical amino acids. CXCL8 from non-human primates (*macaca* mulata, cynomolgus monkey) share 95% identity (73 of 77 amino acids identical) with human CXCL8. There is no ortholog of CXCL8 in mice and rats.

Of course, because the CXCL8 binding nucleic acids molecule according to the present invention interacts with or binds to human CXCL8, a skilled person will generally understand that the CXCL8 binding nucleic acid molecule according to the present invention can easily be used for the treatment, prevention and/or diagnosis of any disease of humans and animals as described herein. In connection therewith, it is to be acknowledged that the nucleic acid molecules according to the present invention can be used for the treatment and/or prevention of any of the diseases, disorder or condition described herein, irrespective of the mode of action underlying such disease, disorder and condition.

In the following, and without wishing to be bound by any theory, the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the CXCL8-CXCL8 receptor axis as outlined in connection therewith said axis may be addressed by the nucleic acid molecules according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

CXCL8 and its receptors are implicated or involved in the pathophysiology of several inflammatory diseases and the potential of inhibiting CXCL8 for the treatment of such inflammatory diseases is supported by animal disease models. Inflammatory disease and/or disorders and/or diseased conditions for the treatment and/or prevention of which the medicament according to the present invention may be used include, but are not limited to:

Inflammatory Diseases of the Respiratory System
   a. Chronic obstructive pulmonary disorder
   b. Acute respiratory distress syndrome
   c. Asthma and allergic inflammation
   d. Bronchitis, bronchiolitis, bronchiolitis obliterans, bronchiectasis
   e. Interstitial lung diseases, including pulmonary fibrosis
   f. Cystic fibrosis
   g. Lung transplantation
   h. Lung injuries caused by physical insults, e.g. cigarette smoke, reexpansion after callaps, hyperoxia
   i. Lung injuries caused by bacterial, viral or fungal infection (pneumonia)

Inflammatory Diseases of the Skin
   a. Neutrophilic dermatoses
   b. Psoriasis
   c. Bullous pemphigoid
   d. Epidermolysis bullosa
   e. Hidradenitis suppurativa
   f. Neurodermatitis
   g. Excema Autoimmune Diseases
   a. Inflammatory bowel diseases
   b. Ulcerative colitis
   c. Multiple sclerosis
   d. Rheumatoid arthritis
   e. Type 1 diabetes
   f. Ankylosing spondylitis Neurological Diseases
   a. Neuro-sweet disease
   b. Alzheimer disease Ischemia Reperfusion Injuries
   a. Stroke
   b. Myocardial infarction
   c. Cerebral ischemia and infarction Other Inflammatory Diseases
   a. Atherosclerosis
   b. Pancreatic islet transplant rejection
   c. Organ transplant rejection and/or delayed function
   d. Spinal cord injury
   e. Cystitis (reviewed by Russo, Expert Rev Clin Immunol 2014 and Ha, Theranostics 2017).

CXCL8 is overexpressed in human cancers and experimental cancer models support the potential of inhibiting CXCL8 for the treatment of cancer. Accordingly, disease and/or disorders and/or diseased conditions for the treatment and/or prevention of which the medicament according to the present invention may be used include, but are not limited to
   a. lung cancer
   b. colon cancer
   c. colorectal cancer
   d. prostate cancer, including hormone refractory prostate cancer
   e. pancreatic cancer
   f. liver cancer
   g. breast cancer
   h. ovarian cancer
   i. thyroid cancer
   j. melanoma
   k. glioblastoma
   l. osteosarcoma
   m. esophageal cancer
   n. hematological cancers (leukemias and lymphomas)
   o. PTEN insufficient tumors
   p. P53-mutated tumors
   q. Kras-mutated tumors
   r. Treatment resistant cancers, including cancers resistant to the treatment with chemotherapeutic agents, antiangiogenic agents, tyrosine kinase inhibitors and immune checkpoint inhibitors.

In a further embodiment, the medicament comprises a further pharmaceutically active agent for the treatment of cancer and/or tumors. Such further pharmaceutically active compounds are, among others but not limited thereto, those known to antineoplastic-active substances as alkylating agents, antimetabolites, antiangiogenic agents, mitose inhibiting agents, topoisomerase inhibitors, inhibitors of the cellular signal transduction, hormones, antibodies, immune conjugates and fusion proteins.

Other pharmaceutically active compounds for the treatment of cancer and/or tumors are immunotherapeutic agents. Such further pharmaceutically active compounds are, among others but not limited thereto, checkpoint inhibitors, cancer vaccines, immune-stimulating agents, cellular, cancer therapies.

Other pharmaceutically active compounds are, among others but not limited thereto, those known to Bleomycin, inhibitors of thymidylatsynthase such as Raltitrexed and Pemetrexed, enzymes such as L-asparaginase, Miltefosin and ANAgrelid, inhibitors of the proteasome such as Bortezomib.

It is within the present invention that the medicament and pharmaceutical composition, respectively, containing a nucleic acid according to the present inventors may be used for the treatment in such way.

In a further embodiment, the medicament comprises a further pharmaceutically active agent for the treatment of inflammatory diseases. Such further pharmaceutically active compounds are, among others but not limited thereto, those known to suppress the immune system such as non-steroidal anti-inflammatory drugs, corticosteroids, calcineurin inhibitors, cyclosporin A, methotrexate, azathioprin, tacrolimus, rapamycin, chlorambucil, leflunomide, mycophenolate mofetil, brequinar, mizoribin, thalidomide, deoxyspergualin, dapson, hydroxychloroquine, sulfasalazine, anti-histamines, or anti-inflammatory biologics like anti-tumor necrosis factor antibody adalimumab, B cell-depleting anti-CD20 antibody rituximab, anti-IL6R antibody tocilizumab, anti-IgE antibody omalizumab, and intravenous immunoglobulins.

Finally, the further pharmaceutically active agent may be a modulator of the activity of any other chemokine which can be a chemokine agonist or antagonist or a chemokine receptor agonist or antagonist. Alternatively, or additionally, such further pharmaceutically active agent is a further nucleic acid molecule according to the present invention. Alternatively, the medicament comprises at least one more nucleic acid which binds to a target molecule different from CXCL8 or exhibits a function which is different from the one of the nucleic acids according to the present invention.

It is within the present invention that the medicament is alternatively or additionally used, in principle, for the prevention of any of the diseases disclosed in connection with the use of the medicament for the treatment of said diseases. Respective markers therefore, i.e. for the respective diseases are known to the ones skilled in the art. Preferably, the respective marker is CXCL8.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents. Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiancy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an effective amount of the active component(s) of the therapy, including, but not limited to, a nucleic acid molecule of the present invention, dissolved or dispersed in a pharmaceutically acceptable medium.

Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament or a pharmaceutical composition will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament or a pharmaceutical composition required to disperse the active compounds is typically utilized. Suitable regimes for administration are also variable but would be typified by initially administering the compound and monitoring the results and then giving further controlled doses at further intervals.

For instance, for oral administration in the form of a tablet or capsule (e.g., a gelatin capsule), the active drug component, i.e. a nucleic acid molecule of the present invention and/or any further pharmaceutically active agent, also referred to herein as therapeutic agent(s) or active compound(s) can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament or the pharmaceutical composition of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicament, pharmaceutical composition, and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicament, pharmaceutical composition and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and cross—linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecule, medicament or pharmaceutical composition, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 µM in the treatment of any of the diseases disclosed herein.

The nucleic acid molecule, medicament and pharmaceutical composition, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acid molecules according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of CXCL8 in inflamed regional skin lesions. Therefore, a further condition or disease for the treatment or prevention of which the nucleic acid, the medicament and/or the pharmaceutical composition according to the present invention can be used, is inflamed regional skin lesions.

Of course, because a CXCL8 binding nucleic acid molecule according to the present invention interact with or bind to human CXCL8, a skilled person will generally understand that the CXCL8 binding nucleic acid molecule according to the present invention can easily be used for the detection of CXCL8 and for the manufacture of a diagnostic or a biosensor.

As preferably used herein a diagnostic or diagnostic agent or diagnostic means or a biosensor is suitable to detect, either directly or indirectly CXCL8, preferably CXCL8 as described herein and more preferably CXCL8 as described herein relating to the various disorders and diseases described herein. The diagnostic or biosensor is suitable for but not limited to the detection and/or follow-up of any of the disorders and diseases, respectively, described herein. Such detection is possible through the binding of the nucleic acid according to the present invention to CXCL8. Such binding can be detected either directly or indirectly, whereby the nucleic acid molecule may comprise a modification group or may not comprise a modification group. In one preferred embodiment the modification group allows immobilization of the nucleic acid. In another preferred embodiment the modification group is a label. The respective methods and means are known to the ones skilled in the art.

In an embodiment, the inventive nucleic acid is immobilized to the surface of a reaction vessel of the diagnostic, to the surface of a device contained in a reaction vessel of the diagnostic or to the surface of the biosensor, by any means known to the ones skilled in the art including non-covalent or covalent linkages.

In a preferred embodiment the nucleic acid according to the present invention is immobilized by covalent linkage to a surface. Therefore, it is within the present invention that the nucleic acid molecule of the present invention comprises a modification group which allows immobilization of the nucleic acid molecule to surfaces. Such modifications group for covalent binding include, but are not limited to (activated) carboxyl, hydroxyl, phosphatidyl, sulfonic ester, amine, thiol, epoxide, alkyne, strained cycloalkyne (e.g. dibenzocyclooctyl, DBCO; bicyclo[6.1.0]non-4-yne, BCN; or azadibenzocyclooctyne, ADIBO), maleimide, azide, hydrazide.

Such covalent linkages can be formed for example by activated carboxyl groups (e.g. EDC/NHS activation) reacting with primary amines, by maleimide reacting with thiol groups, by copper-catalyzed azide alkyne cycloaddition (click chemistry), by copper-free click chemistry including but not limited to copper-free azide strained alkyne cycloaddition, alkene azide [3+2]cycloaddition, alkene tetrazine inverse-demand Diels-Alder, and alkene tetrazole photo-click reaction, or by direct coupling of thiolated probes on gold surfaces. It is within the embodiment that such methods are not restricted to a particular geometry and that a reactive group can be located on either the surface or the nucleic acids.

In a preferred embodiment, inventive nucleic acids are coupled to azide functionalized surfaces of biosensors by strain-promoted azide-alkyne cycloaddition (click chemistry). For this the surface is functionalized with azide and the oligonucleotide is functionalised with a strained alkyne, e.g. dibenzocyclooctyl, DBCO; bicyclo[6.1.0]non-4-yne (BCN), and azadibenzocyclooctyne (ADIBO), preferably at a 5' or a 3' end. Alternatively, inverse geometry may be used, i.e. using a strained alkyne functionalized biosensor surface and azide-modified nucleic acids.

In another embodiment the nucleic acid according to the present invention is immobilized by non-covalent linkage. Therefore, it is within the present invention that the nucleic acid molecule of the present invention comprises a modification group which allows immobilization of the nucleic acid molecule to surfaces, whereby the binding is reversable. Such modification groups for non-covalent binding include but are not limited to biotin (binding to avidin, streptavidin or neutravidine), bromo-desoxyuridine (binding to an anti-bromo-desoxyruridine antibody), digoxigenin (binding to an anti-digoxigenin antibody), and oligonulceotides (binding to complementary oligonucleotide). Unblocked 3' ends of oligonucleotides may serve as primers for polymerases or as acceptors for another nucleic acid in a ligase reaction. It is within the embodiment that such methods are not restricted to a particular geometry and that a reactive group can be located on either the surface or the nucleic acids.

It is within the present invention that the nucleic acid molecule of the present invention is not immobilized but is used in solution and comprises a modification group which preferably allows detection of the nucleic acid molecule, herein referred to as label. These labels include but are not limited to biotin (binding to avidin, streptavidin or neutravidine), bromo-desoxyuridine (binding to an anti-bromo-desoxyruridine antibody), digoxigenin (binding to an anti-digoxigenin antibody), oligonulceotides (binding to complementary oligonucleotide), fluorescent labels (e.g. fluorescein, Cy-3, Cy-5), an electrochemoluminescence labels, radioactive labels, enzymatic labels, UV-labels, colloidal gold, nanoparticles, and chelator molecule labels.

In a further embodiment a nucleic acid molecule of the present invention contains a non-nucleoside, preferably a hydrophilic, linker such as single unit or repeating ethylene glycol, e.g. triethylene glycol (TEG), hexaethylene glycol (HEG) or even polyethylene glycol (PEG), which can join the nucleic acid and the modification group.

Relating to the detection of CXCL8 preferred methods are direct binding of CXCL8, a sandwich binding assay, a competive binding assay or a lateral flow setup.

In an embodiment, CXCL8 is detected by direct binding of an immobilized nucleic acid to CXCL8. Direct binding according to the present invention is a method that only use a nucleic acid according to the present invention, but not a second molecule that interacts with CXCL8.

One format of a sandwich binding assay is the formation of an immobilised complex of CXCL8 and a nucleic acid molecule according to the invention comprising a modification group for immobilization, whereby the complex is immobilized to the surface of the reaction vessel of the diagnostic, to the surface of a device contained in a reaction vessel of the diagnostic or to the surface of the biosensor, whereby preferably said complex is detected. It is within an embodiment that CXCL8 is detected from the complex. A respective detection means which follows this requirement is, for example, any detection means which is specific for that/those part(s) (epitopes) of the CXCL8 not detected by the nucleic acid molecule of the invention and is selected from the group comprising nucleic acids, polypeptides, proteins and antibodies, the generation of which is known to the ones skilled in the art. The methodologies of such sandwich binding assays are known to persons skilled in the art.

It is within the embodiment of a sandwich binding assay that an inverse geometry may be used wherein the detection means described above is immobilized to the surface of the reaction vessel of the diagnostic, to the surface of a device contained in a reaction vessel of the diagnostic or to the surface of the biosensor to form a complex with CXCL8 provided in a sample and the complex is detected by a nucleic acid molecule of the invention. It is within this embodiment, that nucleic acid molecule according to the invention comprises a label or is non-labelled.

Detection of non-labelled nucleic acid molecule may involve the use of a second detection means which is, preferably, also selected from the group comprising nucleic acids, polypeptides, proteins and embodiments in the various embodiments described herein. Such detection means are preferably specific for the nucleic acid according to the present invention.

Finally, it is also within the present invention that the second detection means is detected using a third detection means, preferably the third detection means is linked to an enzyme, more preferably showing an enzymatic reaction upon detection of the second detection means, or the third detection means is a means for detecting radiation, more preferably radiation emitted by a radionuclide. Preferably, the third detection means is specifically detecting and/or interacting with the second detection means.

In a further embodiment, binding of the nucleic acid molecules according to the invention to CXCL8 is detected in competitive assays. Herein immobilized oligonucleotide probes complementary to parts of the nucleic acid molecules according to the invention compete with complex formation between the inventive nucleic acid and CXCL8, whereby in such embodiment the nucleic acid molecule is not immobilized to a surface. Alternatively, immobilized CXCL8 compete with complex formation between the inventive nucleic acid and CXCL8, whereby in such embodiment the nucleic acid molecule is not immobilized to a surface. In a further embodiment the nucleic acid molecule according to the invention is immobilized to a surface and the binding of CXCL8 to the immobilized nucleic acid molecule according to the invention is competed by oligonucleotide probes complementary to parts of the nucleic acid molecules according to the invention. The methodologies of such assays are known to persons skilled in the art.

Relating to the detection of CXCL8 a further preferred embodiment is the use of the nucleic acid molecules according to the invention for the manufacturing a biosensor. By definition, a biosensor is an analytical device used for the detection of an analyte such as CXCL8, that combines a biological component such as the nucleic acid according to the present invention with a physicochemical detector. The transducer or the detector element, which transforms one signal into another one, works in a physicochemical way: optical, piezoelectric, electrochemical, electrochemiluminescence etc., resulting from the interaction of the CXCL8 with the biological element. The biosensor may comprise at least one biological element covalently immobilized on a biosensor surface. The at least one biological element covalently immobilized on a biosensor surface is a nucleic acid according to the invention comprising a modification group for immobilization, a means with specific binding for that/those epitopes of CXCL8 that are not bound by the inventive nucleic acids, an oligonucleotide probe complementary to the inventive nucleic acids, or CXCL8. If the nucleic acid of the present invention is not immobilized to the surface of the biosensor the nucleic acid of the present invention comprises a modification group that is a label or does not comprise a modification group.

The biosensor surface or the surface of the diagnostic may be selected from the group consisting of gold, silver, titanium, zirconium, vanadium, chromium, manganese, cobalt, tungsten, molybdenum, platinum, aluminium, iron, steel, copper, nickel, silicon, germanium, indium phosphide, gallium arsenide, and oxides, nitrides or alloys or mixtures of the aforementioned materials, indium-tin oxide, glassy carbon, sapphire, and silicate or borate glasses.

These surfaces may further be modified by polylysine, aminosilane, epoxysilane, nitrocellulose, carboxydextran, carbon nanomembranes, graphene oxide, amino graphene, carbon surfaces such as carbon black, carbon fiber, carbon plates, carbon cloth, activated carbon, vitreous carbon, charcoal, activated charcoal, graphite powder, graphite fibers, carbon nanotubes, fullerenes, carboxyl groups, azide groups, thiol groups, hydroxy groups, epoxide, maleimide, alkynes, strained alkynes or combinations thereof.

In a preferred embodiment, a nucleic acid molecule according to the invention comprising a modification group for immobilization is immobilized to the biosensor surface for the direct detection of CXCL8 or for the detection of CXCL8 in a sandwich assay format or a competitive assay format. In another preferred embodiment a detection means specific for that/those epitopes of CXCL8 not detected by the inventive nucleic acid (described above), an oligonucleotide probe complementary to the inventive nucleic acids or CXCL8 is immobilized to the biosensor surface and the a labelled or non-labelled nucleic acids according to the invention (described above) is used for detection in sandwich assay format or a competitive assays format.

Detection systems in diagnostic means and biosensors could be based, e.g. on optical readout (fluorescence, absorption and luminescence), mass change (e.g., quartz crystal microbalance, microelectromechanical systems), refractory index (surface plasmon resonance, ring resonators, ellipsometry), charge (electrochemical impedance, voltammetry, amperometry, potentiometry, or conductivity, field effect transistors), surface stress (cantilever biosensors) and atomic force microscopy.

In a further embodiment a nucleic acid molecule according to the invention is used in sandwich or competitive lateral flow assays. The methodologies of such lateral flow assays are known to persons skilled in the art.

In a further embodiment, binding of a nucleic acid molecule according to the invention to CXCL8 is detected in homogenous assays by nucleic acid probes complementary to parts of the nucleic acid molecule according to the invention, whereby in such embodiment the nucleic acid molecule is not immobilized to a surface. Herein hybridization results in changes of the fluorescence signal of two fluorophoric groups linked to the nucleic acids, preferably a change in the intensity and hybridization competes with complex formation between the inventive nucleic acid and CXCL8. The two fluorophoric groups are either both linked to the nucleic acid probe (molecular beacon) or one is linked to the probe and one is linked to the inventive nucleic acid. In a further embodiment one or two fluorophoric groups are linked to the inventive nucleic acid and complex formation with CXCL8 results in changes of the fluorescence signal, preferably a change in the intensity. The methodologies of such assays are known to persons skilled in the art.

The nucleic acid molecule according to the invention may further be used as starting material for drug design. Basically, there are two possible approaches. One approach is the screening of compound libraries whereas such compound libraries are preferably low molecular weight compound libraries. In an embodiment, the screening is a high throughput screening.

Preferably, high throughput screening is the fast, efficient, trial-and-error evaluation of compounds in a target-based assay. In best case the analyses are carried by a colorimetric measurement. Libraries as used in connection therewith are known to the one skilled in the art.

Alternatively, the nucleic acid molecule according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of a nucleic acid moelcuel according to the present invention and involves a structure, preferably a three-dimensional structure, which is similar to the structure of the inventive nucleic acids or identical to the binding mediating parts of the structure of the inventive nucleic acid. In any case such structure still shows the same or a similar binding characteristic as the inventive nucleic acid. In either a further step or as an alternative step in the rational design of drugs the preferably three-dimensional structure of those parts of the nucleic acid binding to the neurotransmitter are mimicked by chemical groups which are different from nucleotides and nucleic acids. By this mimicry a compound different from the nucleic acid according to the invention can be designed. Such compound is preferably a small molecule or a peptide.

In case of screening of compound libraries, such as by using a competitive assay which are known to the one skilled in the arts, appropriate CXCL8 analogues, CXCL8 agonists or CXCL8 antagonists may be found. Such competitive assays may be set up as follows. The inventive nucleic acid, preferably a Spiegelmer which is a target binding L-nucleic acid, is coupled to a solid phase. In order to identify CXCL8 analogues labelled CXCL8 may be added to the assay.

A potential analogue would compete with the CXCL8 molecules binding to the Spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acid molecules. Additionally, the kit may comprise at least one or several positive or negative controls. A positive control may, for example, be CXCL8, particularly the one against which the inventive nucleic acid is selected or to which it binds, preferably, in liquid form. A negative control may, e.g., be a peptide which is defined in terms of biophysical properties similar to CXCL8 but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

The pharmaceutical and bioanalytical determination of a nucleic acid molecule according to the present invention is elementary for the assessment of its pharmacokinetic and biodynamic profile in several tumours, tissues and organs of the human and non-human body. For such purpose, any of the detection methods disclosed herein or known to a person skilled in the art may be used. In a further aspect of the present invention a sandwich hybridisation assay for the detection of the nucleic acid according to the present invention is provided. Within the detection assay a capture probe and a detection probe are used. The capture probe is complementary to the first part and the detection probe to the second part of the nucleic acid according to the present invention. Both, capture and detection probe, can be formed by DNA nucleotides, modified DNA nucleotides, modified RNA nucleotides, RNA nucleotides, LNA nucleotides and/or PNA nucleotides.

Hence, the capture probe comprise a sequence stretch complementary to the 5'-end of the nucleic acid molecule according to the present invention and the detection probe comprise a sequence stretch complementary to the 3'-end of the nucleic acid molecule according to the present invention. In this case the capture probe is immobilised to a surface or matrix via its 5'-end whereby the capture probe can be immobilised directly at its 5'-end or via a linker between of its 5'-end and the surface or matrix. However, in principle the linker can be linked to each nucleotide of the capture probe. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

Alternatively, the capture probe comprises a sequence stretch complementary to the 3'-end of the nucleic acid molecule according to the present invention and the detection probe comprise a sequence stretch complementary to the 5'-end of the nucleic acid molecule according to the present invention. In this case the capture probe is immobilised to a surface or matrix via its 3'-end whereby the capture probe can be immobilised directly at its 3'-end or via a linker between of its 3'-end and the surface or matrix. However, in principle, the linker can be linked to each nucleotide of the sequence stretch that is complementary to the nucleic acid according to the present invention. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The number of nucleotides of the capture and detection probe that may hybridise to the nucleic acid molecule according to the present invention is variable and can be dependent from the number of nucleotides of the capture and/or the detection probe and/or the nucleic acid according to the present invention itself. The total number of nucleotides of the capture and the detection probe that may hybridise to the nucleic acid according to the present invention should be maximal the number of nucleotides that are comprised by the nucleic acid according to the present invention. The minimal number of nucleotides (2 to 10 nucleotides) of the detection and capture probe should allow hybridisation to the 5'-end or 3'-end, respectively, of the nucleic acid according to the present invention. In order to realize high specificity and selectivity between the nucleic acid according to the present invention and other nucleic acids occurring in samples that are analyzed the total number of nucleotides of the capture and detection probe should be or maximal the number of nucleotides that are comprised by the nucleic acid molecule according to the present invention.

Moreover, the detection probe preferably carries a marker molecule or label that can be detected as previously described herein. The label or marker molecule can in principle be linked to each nucleotide of the detection probe. Preferably, the label or marker is located at the 5'-end or 3'-end of the detection probe, whereby between the nucleotides within the detection probe that are complementary to the nucleic acid molecule according to the present invention, and the label a linker can be inserted. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The detection of the nucleic acid according to the present invention can be carried out as follows: A nucleic acid molecule according to the present invention hybridises with one of its ends to the capture probe and with the other end to the detection probe. Afterwards unbound detection probe is removed by, e.g., one or several washing steps. The amount of bound detection probe which preferably carries a label or marker molecule, can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ. ID. Nos: the chemical nature of the nucleic acid molecules according to the present invention and the target molecules CXCL8 as used herein, the actual sequence thereof and the internal reference number is summarized in the following table.

TABLE 1

| SEQ. ID. NO: | | Name | Sequence (N-terminus→C-terminus) |
|---|---|---|---|
| 1 | D-amino acids | D-CXCL8 (c-bio) (also referred to as "biotinylated D-CXCL8") | AVLPRSAKELRCQCIKTYSKPFHPKFIKELRVIESGPHCANTEIIVKLSDGRELCLD PKENWVQRVVEKFLKRAENS-biotin |
| 2 | L-amino acids | CXCL8 also referred to as "L-CXCL8" | AVLPRSAKELRCQCIKTYSKPFHPKFIKELRVIESGPHCANTEIIVKLSDGRELCLD PKENWVQRVVEKFLKRAENS |

| SEQ ID NO: | | Name | Sequence (5'→3') |
|---|---|---|---|
| 3 | D-RNA | 315-H9-001 | GCUGACGGAAGUACGUGGAAAGCCAAUGAGUGUCCCGGUCAGC |
| 4 | D-RNA | 315-F11-001 | GCUGACGGAAGUACGUGGAAAGCCGAUGAGUGUCCCGGUGAGC |
| 5 | D-RNA | 315-F8-001 | GCUGACGGAAGUACGUGGAAAGCCGAAAGUGUCCCGGUCAGC |
| 6 | D-RNA | 315-F8-002 | CUGACGGAAGUACGUGGAAAGCCGAAAGUGUCCCGGUCAG |
| 7 | D-RNA | 315-F8-003 | UGACGGAAGUACGUGGAAAGCCGAAAGUGUCCCGGUCA |
| 8 | D-RNA | 315-F8-004 | GACGGAAGUACGUGGAAAGCCGAAAGUGUCCCGGUC |
| 9 | D-RNA | 315-F8-005 | GUGACGGAAGUACGUGGAAAGCCGAAAGUGUCCCGGUCAC |
| 10 | D-RNA | 315-F8-006 | GGACGGAAGUACGUGGAAAGCCGAAAGUGUCCCGGUCC |
| 11 | D-RNA | 315-F8-007 | GCACGGAAGUACGUGGAAAGCCGAAAGUGUCCCGGUGC |
| 12 | D-RNA | 315-F8-008 | GGUCGGAAGUACGUGGAAAGCCGAAAGUGUCCCGGACC |
| 13 | D-RNA | 315-F8-009 | UGGCGGAAGUACGUGGAAAGCCGAAAGUGUCCCGGCCA |
| 14 | L-RNA | 315-H9-001 | GCUGACGGAAGUACGUGGAAAGCCAAUGAGUGUCCCGGUCAGC |
| 15 | L-RNA | 315-F11-001 | GCUGACGGAAGUACGUGGAAAGCCGAUGAGUGUCCCGGUGAGC |
| 16 | L-RNA | 315-F8-001 | GCUGACGGAAGUACGUGGAAAGCCGAAAGUGUCCCGGUCAGC |
| 17 | L-RNA | 315-F8-002 | CUGACGGAAGUACGUGGAAAGCCGAAAGUGUCCCGGUCAG |
| 18 | L-RNA | 315-F8-003 | UGACGGAAGUACGUGGAAAGCCGAAAGUGUCCCGGUCA |
| 19 | L-RNA | 315-F8-004 | GACGGAAGUACGUGGAAAGCCGAAAGUGUCCCGGUC |
| 20 | L-RNA | 315-F8-005 | GUGACGGAAGUACGUGGAAAGCCGAAAGUGUCCCGGUCAC |
| 21 | L-RNA | 315-F8-006 | GGACGGAAGUACGUGGAAAGCCGAAAGUGUCCCGGUCC |

TABLE 1-continued

| | | Name | |
|---|---|---|---|
| 22 | L-RNA | 315-F8-007 | GCACGGAAGUACGUGGAAAGCCGAAAGUGUCCCGGUGC |
| 23 | L-RNA | 315-F8-008 | GGUCGGAAGUACGUGGAAAGCCGAAAGUGUCCCGGACC |
| 24 | L-RNA | 315-F8-009 | UGGCGGAAGUACGUGGAAAGCCGAAAGUGUCCCGGCCA |
| 25 | L-RNA | 315-F8-002-PEG, 315-F8-002-5'-PEG | PEG-Linker-CUGACGGAAGUACGUGGAAAGCCGAAAGUGUCCCGGUCAG; Linker = aminohexyl |
| 26 | L-RNA | 315-F8-002-Amino, 315-F8-002-5'-Amino | NH2-Linker-CUGACGGAAGUACGUGGAAAGCCGAAA1GUGUCCCGGUCAG; |
| 27 | | | GGAAGUACGUGGAAAGCCRA($X_U$)RAGUGUGUCCCG wherein $X_U$ is U or absent |
| 28 | | | GGAAGUACGUGGAAAGCCAAUGAGUGUGUCCCG |
| 29 | | | GGAAGUACGUGGAAAGCCGAUGAGUGUGUCCCG |
| 30 | | | GGAAGUACGUGGAAAGCCGAAAGUGUGUCCCG |
| 31 | | reverse 315-F8-002-Amino | NH2-Linker-GACUGGCCCUGUGUGUUGAAAGCCGAAAGGUCGAUGAAGGCAGUC |

| SEQ ID NO: | | Name | Sequence (N-terminus→C-terminus) |
|---|---|---|---|
| 32 | L-amino acids | CXCL1 | ASVATELRCQCLQTLQGIHPKNIQSVNVKSPGPHCAQTEVIATLKNGRKACLNPASPIVKKIIEKMLNSDKSN |
| 33 | L-amino acids | CXCL2 | APLATELRCQCLQTLQGIHLKNIQSVKVKSPGPHCAQTEVIATLKNGQKACLNPASPMVKKIIEKMLKNGKSN |
| 34 | L-amino acids | CXCL3 | ASVVTELRCQCLQTLQGIHLKNIQSVNVRSPGPHCAQTEVIATLKNGKKACLNPASPMVQKIEKILNKGSTN |
| 35 | L-amino acids | CXCL5 | AGPAAAVLRELRCVCLQTTQGVHPKMISNLQVFAIGPQCSKVEVVASLKNGKEICLDPEAPFLKKVIQKILDGGNKEN |
| 36 | L-amino acids | CXCL6 | GPVSAVLTELRCTCLRVTLRVNPKTIGKLQVPPAGPQCSKVEVVASLKNGKQVCLDPEAPFLKKVIQKILDSGNKKN |
| 37 | L-amino acids | CXCL7 | SSTKGQTKRNLAKGKEESLDSDLYAELRCMCIKTTSGIHPKNIQSLEVIGKGTHCNQVEVIATLKDGRKICLDPDAPRIKKIVQKKLAGDESAD |
| 38 | L-amino acids | CCL5 | SPYSSDTTPCCFAYIARPLPRAHIKEYFYTSGKCSNPAVVFVTRKNRQVCANPEKKWVREYINSLEMS |

TABLE 1-continued

| SEQ. ID. NO: | | Name | Sequence (5'→3') |
|---|---|---|---|
| 39 | L-RNA | 315-F8-002-3'-PEG | CUGACGGAAGUACGUGGAAGCCGAAAGUGUCCGGUCAG-Linker-PEG; Linker = aminohexyl |
| 40 | L-RNA | 315-F8-002-3'-Amino | CUGACGGAAGUACGUGGAAGCCGAAAGUGUCCCGGUCAG-Linker-Amino; Linker = aminohexyl |
| 41 | L-RNA | 315-F8-005-5'-PEG | PEG-Linker-GUGACGGAAGUACGUGGAAAGCCGAAAGUGUCCGGUCAC; Linker = aminohexyl |
| 42 | L-RNA | 315-F8-005-5'-Amino | NH2-Linker-GUGACGGAAGUACGUGGAAAGCCGAAAGUGUCCCGGUCAC; Linker = aminohexyl |
| 43 | L-RNA | 315-F8-005-3'-PEG | GUGACGGAAGUACGUGGAAAGCCGAAAGUGUCCCGGUCAC-Linker-PEG; Linker = aminohexyl |
| 44 | L-RNA | 315-F8-005-3'-Amino | GUGACGGAAGUACGUGGAAAGCCGAAAGUGUCCCGGUCAC-Linker-Amino; Linker = aminohexyl |
| 45 | D-RNA | 8A-35 (Sung, Biomaterials 2014) | 5'-GGGGGCUUAUCAUUCCAUUUAGUGUUAUGAUAACC-3' C = 2'Fluoro-C; U = 2'Fluor-U |

PEG = Y-shape 40kD-polyethylene glycol

The features of the present invention disclosed in the specification, the claims, the sequence listing and/or the drawings may both separately and in any combination thereof be material for realizing the invention in various forms thereof.

The present invention is further illustrated by the figures, examples and the sequence listing from which further features, embodiments and advantages may be taken, wherein FIG. 1 shows an alignment of sequences of nucleic acid molecules capable of binding human CXCL8 including the $K_D$ value determined by competition pull-down binding assay (315-H9-001, SEQ ID NO:3; 315-F11-001, SEQ ID NO:4, 315-F8-001, SEQ ID NO:5);

FIG. 2 shows truncated derivatives of nucleic acid molecule 315-F8-001 including the $K_D$ value and relative binding activity to human CXCL8 as determined by determined by competition pull-down binding assay and/or by surface plasmon resonance measurement (315-F8-001, SEQ ID NO:5, 315-F8-002, SEQ ID NO:6, 315-F8-002-PEG, SEQ ID NO:25, 315-F8-003, SEQ ID NO:7, 315-F8-004, SEQ ID NO:8, 315-F8-005, SEQ ID NO:9, 315-F8-006, SEQ ID NO:10, 315-F8-007, SEQ ID NO:11, 315-F8-008, SEQ ID NO:12, 315-F8-009, SEQ ID NO:13);

FIG. 4 shows binding of nucleic acid molecule 315-F8-002 to CXCL8 at (A) 25° C. and (B) 37° C. as determined by surface plasmon resonance measurement. Association constant ka and dissociation constant kd are given;

FIG. 5 shows binding of nucleic acid molecule 315-F8-002-PEG to CXCL8 at (A) 25° C. and (B) 37° C. as determined by surface plasmon resonance measurement. Association constant ka and dissociation constant kd are given;

Figure 8:

FIG. 8 is a bar diagram showing quantification of CXCL8 by nucleic acid molecule 315-F8-002 (FIG. 8A) and quantification of CCL5 by nucleic acid molecule 315-F8-002 (FIG. 8B); and FIG. 9 is a bar diagram showing binding of L-aptamer 315-F8-002 (FIG. 9A) and aptamer 8A-35 (FIG. 9B) to soluble CXCL8 and CXCL1 at different concenctions.

EXAMPLE 1: NUCLEIC ACIDS CAPABLE OF BINDING HUMAN CXCL8

Several CXCL8-binding nucleic acids and derivatives thereof were identified, the nucleotide sequences of which are depicted in FIGS. 1 to 2. CXCL8 binding nucleic acids were tested as D-aptamers (D-nucleic acids) and L-aptamers (L-nucleic acids), whereby the D-nucleic acids and the L-nuclei acids were synthesized as described in Example 2.

CXCL8-binding nucleic acids were characterized a) as D-aptamers by pull-down binding assays to biotinylated D-CXCL8 (SEQ ID NO: 1) as shown in Example 3; and b) as L-aptamers by surface plasmon resonance (SPR) measurement (Example 4), and by an in vitro assay with cells expressing the human CXCR2 receptor, whereby for both methods L-CXCL8 (SEQ ID NO: 2) was used (Example 5).

The nucleic acids thus generated exhibit slightly different sequences, whereby the sequences can be summarized or grouped as a sequence family.

For definition of nucleotide sequence motifs, the IUPAC abbreviations for ambiguous nucleotides are used:

| S | strong | G or C; |
| W | weak | A or U (T); |
| R | purine | G or A; |
| Y | pyrimidine | C or U (T); |
| K | keto | G or U (T); |
| M | imino | A or C; |
| B | not A | C or U (T) or G; |
| D | not C | A or G or U (T); |
| H | not G | A or C or U (T); |
| V | not U | A or C or G; |
| N | all | A or G or C or U (T) |

If not indicated to the contrary, any nucleic acid sequence or sequence of stretches, respectively, is indicated in the 5'→3' direction.

As depicted in FIGS. 1 to 2 CXCL8 binding nucleic acids comprise one central stretch of nucleotides defining a potential CXCL8 binding motif, whereby FIG. 1 shows the different sequences of the sequence family and FIG. 2 show truncated derivatives of the CXCL8 nucleic acid 315-F8-001 including CXCL8 nucleic acid 315-F8-002-PEG.

In general, CXCL8 binding nucleic acid molecules comprise at the 5'-end and the 3'-end terminal stretches of nucleotides: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily given in the molecule in vivo and in vitro.

The three stretches of nucleotides of CXCL8 binding nucleic acid molecules —the first terminal stretch of nucleotides, the central stretch of nucleotides and the second terminal stretch of nucleotides—are arranged to each other in 5'+3'-direction: the first terminal stretch of nucleotides— the central stretch of nucleotides —the second terminal stretch of nucleotides. However, alternatively, the first terminal stretch of nucleotides, the central stretch of nucleotides and the second terminal stretch of nucleotides are arranged to each other in 5'+3'-direction: the second terminal stretch of nucleotides —the central stretch of nucleotides —the first terminal stretch of nucleotides.

The sequences of the defined stretches may be different between the CXCL8 binding nucleic acid molecules which influences the binding affinity to CXCL8. Based on binding analysis of the different CXCL8 binding nucleic acid molecules the central stretch of nucleotides and their nucleotide sequences as described in the following are individually and more preferably in their entirety essential for binding to CXCL8.

The CXCL8 binding nucleic acids consist of ribonucleotides (as shown in FIGS. 1 to 2). As shown in FIG. 1 the sequence of the central stretch of nucleotides of the CXCL8 binding nucleic acids 315-H9-001, 315-F11-001 and 315-F8-001 are slightly different:

```
5'  GGAAGUACGUGGAAAGCCAAUGAGUGUGUCCCG  3'
    (315-H9-001, SEQ ID NO: 3),
```

-continued

```
5' GGAAGUACGUGGAAAGCCGAUGAGUGUGUCCCG 3'
(315-F11-001, SEQ ID NO: 4),

5' GGAAGUACGUGGAAAGCCGAAAGUGUGUCCCG 3'
(315-F8-001, SEQ ID NO: 5).
```

The central stretch of nucleotides of the CXCL8 binding nucleic acids according to the present invention comprises 32-33 nt and can be summarized in the consensus sequence: 5' GGAAGUACGUGGAAAGCCRA($X_U$)RAGUGUGU-CCCG 3'(SEQ ID NO: 27), wherein $X_U$ is U or absent.

The CXCL8 binding nucleic acids with the best binding affinity to CXCL8, that means the CXCL8 binding nucleic acids with the highest binding affinity to CXCL8 or the lowest dissociation constant Kd for CXCL8, comprise a central stretch of nucleotides with a sequence of 5' GGAAGUACGUGGAAAGCCGAAAGUGUGUCCCG 3'(315-F8-001, SEQ ID NO: 5) and 5' GGAAGUACGUG-GAAAGCCAAUGAGUGUGUCCCG 3'(315-FH9-001, SEQ ID NO: 4) whereby a central stretch of nucleotides with a sequence of 5' GGAAGUACGUGGAAAGCCGAAAGU-GUGUCCCG 3'(315-F8-001, SEQ ID NO: 5) leads to the best binding affinity of a CXCL8 nucleic acid for CXCL8.

As shown in FIGS. 1 and 2 the first terminal stretch of nucleotides and second terminal stretch of nucleotides of CXCL8 binding nucleic acids comprise six nucleotides, five nucleotides, four nucleotides or three nucleotides whereby the stretches optionally hybridize with each other, whereby upon hybridization a double-stranded structure is formed. This double-stranded structure can consist of six, five, four, or three base pairs. However, such hybridization is not necessarily given in the molecule.

As shown in FIG. 1 the first and the second stretch of nucleotides of the CXCL8 binding nucleic acids 315-H9-001, 315-F11-001 and 315-F8-001 comprise six nucleotides, respectively:
 a) CXCL8 binding nucleic acids 315-H9-001 and 315-F8-001—the first terminal stretch of nucleotides comprises a nucleotide sequence of 5' GCUGAC 3' and the second terminal stretch of nucleotides comprises a nucleotide sequence of 5' GUCAGC 3';
 b) CXCL8 binding nucleic acid 315-F11-001—the first terminal stretch of nucleotides comprises a nucleotide sequence of 5' GCUGAC 3' and the second terminal stretch of nucleotides comprises a nucleotide sequence of 5' GUGAGC 3'.

As shown in FIG. 2 the first and the second stretch of nucleotides of the CXCL8 binding nucleic acids comprise five, four or three nucleotides, respectively:
 a) CXCL8 binding nucleic acid 315-F8-002—the first terminal stretch of nucleotides comprises a nucleotide sequence of 5' CUGAC 3' and the second terminal stretch of nucleotides comprises a nucleotide sequence of 5' GUCAG 3';
 b) CXCL8 binding nucleic acid 315-F8-005—the first terminal stretch of nucleotides comprises a nucleotide sequence of 5' GUGAC 3' and the second terminal stretch of nucleotides comprises a nucleotide sequence of 5' GUCAC 3';
 c) CXCL8 binding nucleic acid 315-F8-003—the first terminal stretch of nucleotides comprises a nucleotide sequence of 5' UGAC 3' and the second terminal stretch of nucleotides comprises a nucleotide sequence of 5' GUCA 3';
 d) CXCL8 binding nucleic acid 315-F8-006—the first terminal stretch of nucleotides comprises a nucleotide sequence of 5' GGAC 3' and the second terminal stretch of nucleotides comprises a nucleotide sequence of 5' GUCC 3';
 e) CXCL8 binding nucleic acid 315-F8-007—the first terminal stretch of nucleotides comprises a nucleotide sequence of 5' GCAC 3' and the second terminal stretch of nucleotides comprises a nucleotide sequence of 5' GUGC 3';
 f) CXCL8 binding nucleic acid 315-F8-008—the first terminal stretch of nucleotides comprises a nucleotide sequence of 5' GGUC 3' and the second terminal stretch of nucleotides comprises a nucleotide sequence of 5' GACC 3';
 g) CXCL8 binding nucleic acid 315-F8-009—the first terminal stretch of nucleotides comprises a nucleotide sequence of 5' UGGC 3' and the second terminal stretch of nucleotides comprises a nucleotide sequence of 5' GCCA 3';
 h) CXCL8 binding nucleic acid 315-F8-004—the first terminal stretch of nucleotides comprises a nucleotide sequence of 5' GAC 3' and the second terminal stretch of nucleotides comprises a nucleotide sequence of 5' GUC 3'.

The first terminal stretch of nucleotides and the second terminal stretch of nucleotides of all tested CXCL8 binding nucleic acid molecules can be summarized in the following generic formula for the first terminal stretch of nucleotides and the second terminal stretch of nucleotides: the generic formula for the first terminal stretch of nucleotides is 5' $Z_1Z_2Z_3Z_4Z_5$C 3' and the generic formula for the second terminal stretch of nucleotides is 5' G$Z_6Z_7Z_8Z_9$ $Z_{10}$ 3', wherein $Z_1$ is G or absent, $Z_2$ is S or absent, $Z_3$ is K or absent, $Z_4$ is S, $Z_5$ is D, $Z_6$ is H, $Z_7$ is S, $Z_8$ is M or absent, $Z_9$ is S or absent, and $Z_{10}$ is C or absent,
  whereby in a first preferred embodiment
  q) $Z_1$ is G, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is C; or r) $Z_1$ is absent, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is absent; or
  s) $Z_1$ is absent, $Z_2$ is absent, $Z_3$ is K, $Z_4$ is S, $Z_5$ is D, $Z_6$ is H, $Z_7$ is S, $Z_8$ is M, $Z_9$ is absent, and $Z_{10}$ is absent; or
  t) $Z_1$ is absent, $Z_2$ is absent, $Z_3$ is absent, $Z_4$ is S, $Z_5$ is D, $Z_6$ is H, $Z_7$ is S, $Z_8$ is absent, $Z_9$ is absent, and $Z_{10}$ is absent; or
  u) $Z_1$ is absent, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is C; or
  v) $Z_1$ is absent, $Z_2$ is absent, $Z_3$ is K, $Z_4$ is S, $Z_5$ is D, $Z_6$ is H, $Z_7$ is S, $Z_8$ is M, $Z_9$ is S, and $Z_{10}$ is C; or
  w) $Z_1$ is absent, $Z_2$ is absent, $Z_3$ is absent, $Z_4$ is S, $Z_5$ is D, $Z_6$ is H, $Z_7$ is S, $Z_8$ is M, $Z_9$ is S, and $Z_{10}$ is C; or
  x) $Z_1$ is G, $Z_2$ is S, $Z_3$ is K, $Z_4$ is S, $Z_5$ is D, $Z_6$ is H, $Z_7$ is S, $Z_8$ is M, $Z_9$ is S, and $Z_{10}$ is absent; or
  y) $Z_1$ is G, $Z_2$ is S, $Z_3$ is K, $Z_4$ is S, $Z_5$ is D, $Z_6$ is H, $Z_7$ is S, $Z_8$ is M, $Z_9$ is absent, and $Z_{10}$ is absent; or
  z) $Z_1$ is G, $Z_2$ is S, $Z_3$ is K, $Z_4$ is S, $Z_5$ is D, $Z_6$ is H, $Z_7$ is S, $Z_8$ is absent, $Z_9$ is absent, and $Z_{10}$ is absent; or aa) $Z_1$ is absent, $Z_2$ is S, $Z_3$ is K, $Z_4$ is S, $Z_5$ is D, $Z_6$ is H, $Z_7$ is S, $Z_5$ is M, $Z_9$ is absent, and $Z_{10}$ is absent; or bb) $Z_1$ is absent, $Z_2$ is S, $Z_3$ is K, $Z_4$ is S, $Z_5$ is D, $Z_6$ is H, $Z_7$ is S, $Z_5$ is absent, $Z_9$ is absent, and $Z_{10}$ is absent; or
  cc) $Z_1$ is absent, $Z_2$ is absent, $Z_3$ is K, $Z_4$ is S, $Z_5$ is D, $Z_6$ is H, $Z_7$ is S, $Z_5$ is M, $Z_9$ is S, and $Z_{10}$ is absent; or
  dd) $Z_1$ is absent, $Z_2$ is absent, $Z_3$ is absent, $Z_4$ is S, $Z_5$ is D, $Z_6$ is H, $Z_7$ is S, $Z_5$ is M, $Z_9$ is S, and $Z_{10}$ is absent; or ee) $Z_1$ is absent, $Z_2$ is absent, $Z_3$ is K, $Z_4$ is S, $Z_5$ is D, $Z_6$ is H, $Z_7$ is S, $Z_8$ is absent, $Z_9$ is absent, and $Z_{10}$ is absent; or ff) $Z_1$ is absent, $Z_2$ is absent, $Z_3$ is absent, $Z_4$ is S, $Z_5$ is D, $Z_6$ is H, $Z_7$ is S, $Z_8$ is M, $Z_9$ is absent, and $Z_{10}$ is absent.

The CXCL8 binding nucleic acids with the best binding affinity to CXCL8, that means the CXCL8 binding nucleic acids with the highest binding affinity to CXCL8 or the lowest dissociation constant Kd for CXCL8, comprise the following first and second terminal stretches of nucleotides:

a) CXCL8 binding nucleic acids 315-H9-001 and 315-F8-001—the first terminal stretch of nucleotides comprises a nucleotide sequence of 5' GCUGAC 3' and the second terminal stretch of nucleotides comprises a nucleotide sequence of 5' GUCAGC 3';

b) CXCL8 binding nucleic acid 315-F8-002—the first terminal stretch of nucleotides comprises a nucleotide sequence of 5' CUGAC 3' and the second terminal stretch of nucleotides comprises a nucleotide sequence of 5' GUCAG 3';

c) CXCL8 binding nucleic acid 315-F8-005—the first terminal stretch of nucleotides comprises a nucleotide sequence of 5' GUGAC 3' and the second terminal stretch of nucleotides comprises a nucleotide sequence of 5' GUCAC 3'.

Figure 3:
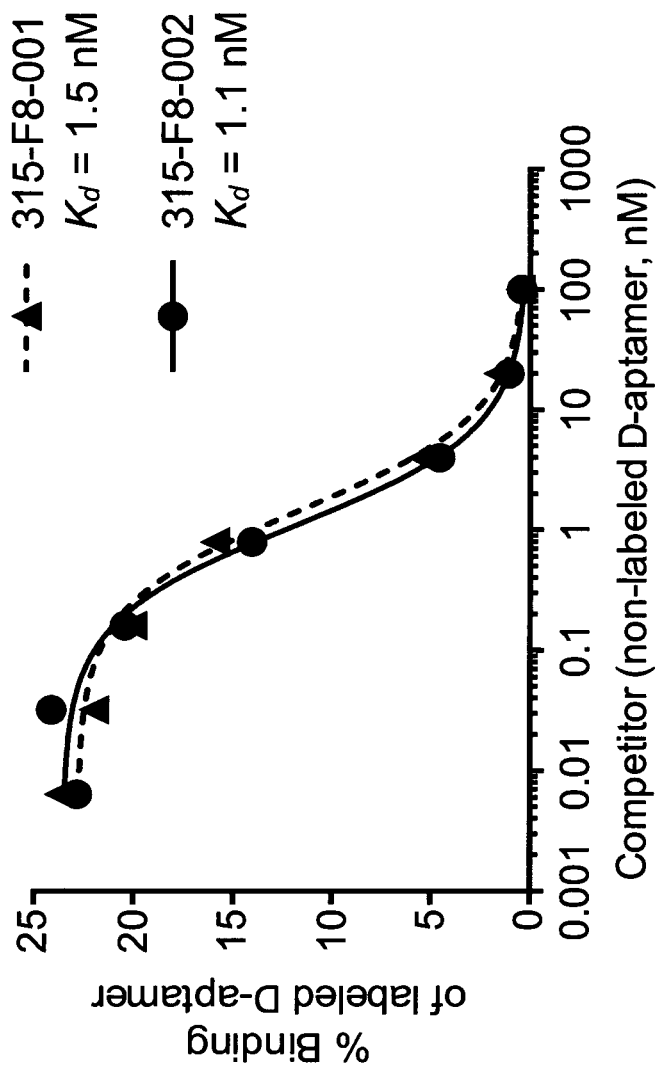
FIG. 3 shows the kinetic evaluation by competition pull-down binding assay of D-nucleic acid molecules 315-F8-001 and 315-F8-002 to D-CXCL8.

The Kd values of CXCL8-binding nucleic acids 315-F8-001, 315-H9-001 and 315-F11-001 (comprising terminal stretches with six nucleotides) were measured in the range of 1.5-12.5 nM as determined in a competition pull-down binding assay (FIGS. 1 to 3). In a direct pull-down assay format CXCL8-binding nucleic acid 315-F8-001 showed a Kd value of 0.8 nM. Using surface plasmon resonance measurement, a more sensitive method for determining Kd values, the Kd for CXCL8 binding nucleic acid 315-F8-001, was 0.22 nM at 25° C. and 0.68 nM at 37° C. (FIG. 2).

It was surprisingly found that truncation of the first terminal stretch from six to five nucleotides and the truncation of the second terminal stretch from six to five nucleotides had no negative effect on the binding affinity to CXCL8. The binding affinity of CXCL8 binding nucleic acid 315-F8-002 as measured by the competition pull-down assay (Kd of 1.1 nM; FIGS. 2 and 3) and by surface plasmon resonance measurement (Kd of 0.22 nM at 25° C. and of 0.75 nM at 37° C.; FIGS. 2 and 4) is in the range of the binding affinity as determined for CXCL8-binding nucleic acid 315-F8-001 (see Kd values for 315-F8-001 supra).

Attempts to further truncate and/or mutate the terminal stretches of CXCL8-binding nucleic acid 315-F8-002 resulted in CXCL8-binding nucleic acids 315-F8-003, 315-F8-004, 315-F8-005, 315-F8-006, 315-F8-007, 315-F8-008 and 315-F8-009 with lower (315-F8-003, 315-F8-004, 315-F8-006, 315-F8-007, 315-F8-008, and 315-F8-009) or similar (315-F8-005) binding affinities for CXCL8 (FIG. 2).

For the 5'-40 kDa-PEGylated variant of CXCL8-binding nucleic acid 315-F8-002, the CXCL8-binding nucleic acid 315-F8-002-PEG (also referred to as AON-S08) a Kd of 0.2 nM at 25° C. and 0.8 nM at 37° C. was determined by surface plasmon resonance measurement (FIGS. 2 and 5).

Figure 6:
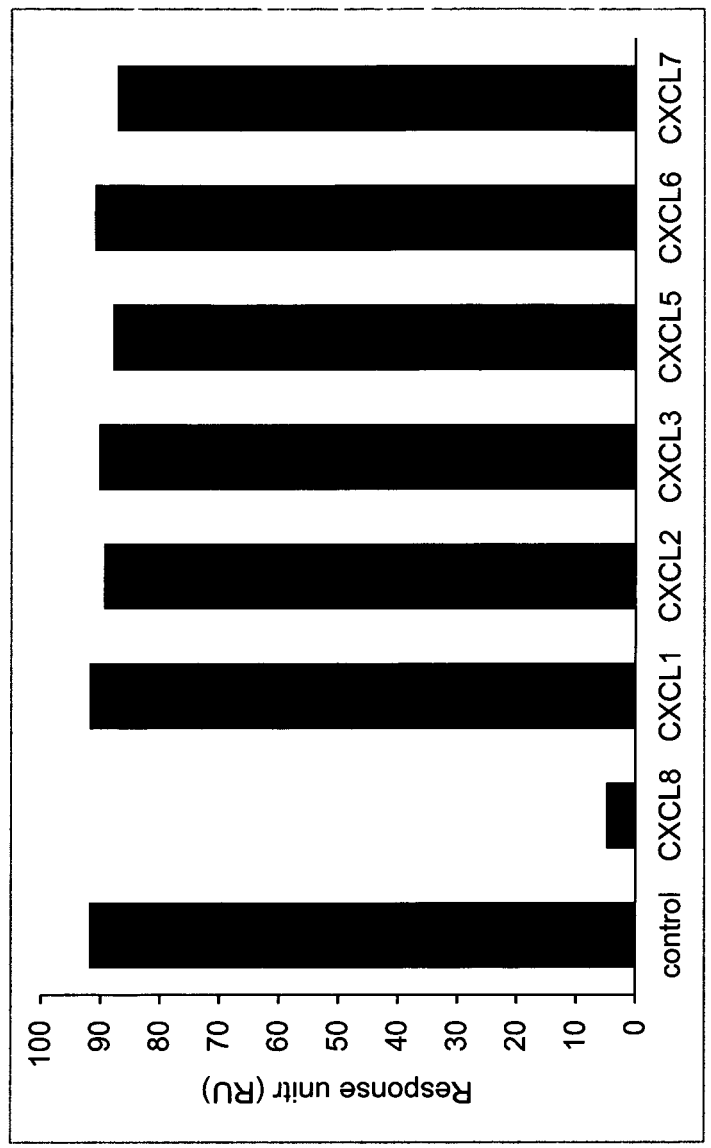
FIG. 6 shows the selectivity of 315-F8-002 binding for CXCL8 as determined by a by a competitive binding assays using surface plasmon resonance measurement.

CXCL8 is one of several ELR-positive human CXC chemokines. Beside CXCL8, the ELR-positive human CXC chemokines CXCL1, CXCL2, CXCL3, CXCL5, CXCL6, CXCL7 bind to the CXCL8 receptor CXCR2, wherein the ELR-positive human CXC chemokines CXCL6 and CXCL7 also bind to the CXCL8 receptor CXCR1. To show the specificity and selectivity of the binding characteristics of CXCL8 binding nucleic acid 315-F8-002, the binding affinity of CXCL8 binding nucleic acid 315-F8-002 to the ELR-positive human CXC chemokines CXCL1, CXCL2, CXCL3, CXCL5, CXCL6, CXCL7 was tested by SPR in a competitive binding assay (Example 4). CXCL8 binding nucleic acid 315-F8-002 showed no binding to any other ELR-positive human CXC chemokine CXCL1, CXCL2, CXCL3, CXCL5, CXCL6, CXCL7 (FIG. 6).

Figure 7:
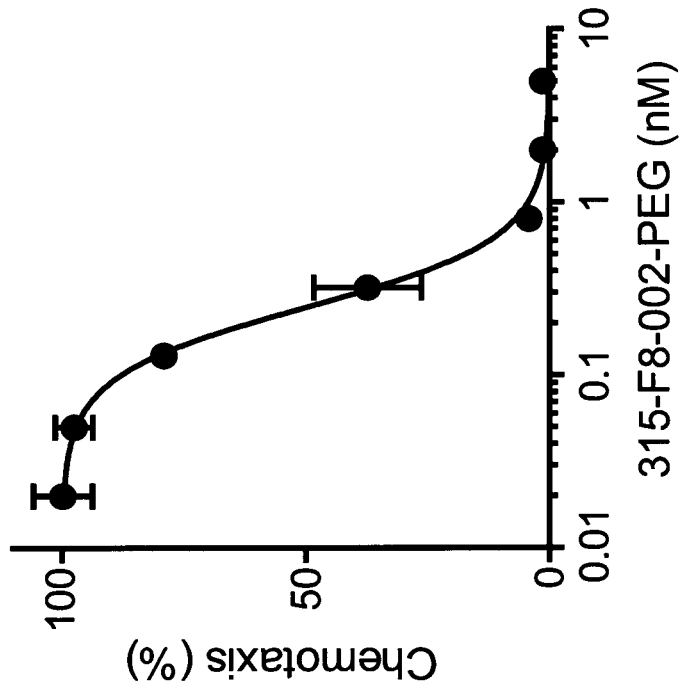
FIG. 7 shows the inhibition of CXCL8-induced chemotaxis of CXCR2-expressing cells by nucleic acid molecule 315-F8-002-PEG.

CXCL8 binding nucleic acid 315-F8-002-PEG inhibited CXCL8-induced chemotaxis of CXCR2-expressing BA/F3 cells with a mean inhibitory constant TC50 of 0.26 nM (FIG. 7, Example 5).

A biosensor with immobilized CXCL8 binding nucleic acid 315-F8-002 was used to detect and quantify CXCL8. The limit of detection (mean baseline value+3× standard deviation of baseline values) was <98 µM CXCL8 and the lower limit of quantification (mean baseline value+10× standard deviation of baseline values) was also<98 µM CXCL8 (FIG. 8A, Example 6). In order to show the specificity of the immobilised CXCL8 binding nucleic acid 315-F8-002, a different chemokine (CCL5) was used as an analyte. No binding of CCL5 was measured at concentrations up to 12.5 nM (FIG. 8B, Example 6).

EXAMPLE 2: SYNTHESIS OF D- AND L-APTAMERS

Small Scale Solid-Phase Synthesis

D-aptamers (D-nucleic acids) and L-aptamers (L-nucleic acids) were produced by solid-phase synthesis with an ABI 394 synthesizer (Applied Biosystems, Foster City, CA, USA) using 2'TBDMS RNA phosphoramidite chemistry (Damha and Ogilvie, 1993). L-rA(N-Bz)-, L-rC(Ac)-, L-rG (N-ibu)-, L-rU-, D-rA(N-Bz)-, D-rC(Ac)-, D-rG(N-ibu)-, D-rU-phosphoramidites were purchased from ChemGenes, Wilmington, MA. D- and L-aptamers were purified by gel electrophoresis.

Large Scale Solid-Phase Synthesis

L-aptamers were produced by solid-phase synthesis with an ÄktaPilot100 synthesizer (Amersham Biosciences; General Electric Healthcare, Freiburg) using 2'TBDMS RNA and DNA phosphoramidite chemistry (Damha and Ogilvie, 1993). L-rA(N-Bz)-, L-rC(Ac)-, L-rG(N-ibu)-, and L-rU-were purchased from ChemGenes, Wilmington, MA. The 5'-amino-modifier was purchased from American International Chemicals Inc. (Framingham, MA, USA). Synthesis of the unmodified or 5'-amino-modified L-aptamer was started on L-riboA, L-riboC, L-riboG, or L-riboU, modified CPG pore size 1000 Å (Link Technology, Glasgow, UK. For coupling of the RNA phosphoramidites (15 min per cycle), 0.3 M benzylthiotetrazole (CMS-Chemicals, Abingdon, UK) in acetonitrile, and 2 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The L-aptamer was synthesized DMT-ON; after deprotection, it was purified via preparative RP-HPLC (Wincott et al., 1995) using Source15RPC medium (Amersham). The 5'DMT-group was removed with 80% acetic acid (30 min at RT). In case of 5'aminomodified L-aptamers the 5'MMT-group was removed with 80% acetic acid (90 min at RT). Subsequently, aqueous 2 M NaOAc solution was added and the L-aptamer was desalted by tangential-flow filtration using a 5 K regenerated cellulose membrane (Millipore, Bedford, MA).

PEGylation of L-aptamers

To prolong the L-aptamer's plasma residence time in vivo, the L-aptamer was covalently coupled to a 40 kDa polyethylene glycol (PEG) moiety at 5'-end. For PEGylation (for technical details of the method for PEGylation see European patent application EP 1 306 382), the purified 5' amino modified L-aptamer was dissolved in a mixture of $H_2O$ (2.5 ml), DMF (5 ml), and buffer A (5 ml; prepared by mixing citric acid $H_2O$ [7 g], boric acid [3.54 g], phosphoric acid [2.26 ml], and 1 M NaOH [343 ml] and adding water to a final volume of 1l; pH=8.4 was adjusted with 1 M HCl).

The pH of the L-aptamer solution was brought to 8.4 with 1 M NaOH. Then, 40 kDa PEG-NHS ester (Jenkem Technology, Allen, TX, USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated L-aptamer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated L-aptamer at 10-15% buffer C. Product fractions with a purity of >95% (as assessed by HPLC) were combined and mixed with 40 ml 3 M NaOAc. The PEGylated L-aptamer was desalted by tangential-flow filtration (5 K regenerated cellulose membrane, Millipore, Bedford MA).

EXAMPLE 3: PULL-DOWN BINDING ASSAYS

Direct Pull-Down Assay for Determination of Binding Constants of D-Aptamers Direct pull-down assays are used to determine the affinity of D-aptamers to D-CXCL8(C-bio) (SEQ ID NO: 1). For this purpose, D-aptamers are radioactively labeled by T4 polynucleotide kinase (Invitrogen, Karlsruhe, Germany) using [$\gamma$-$^{32}$P]-ATP (Hartmann Analytic, Braunschweig, Germany). The specific radioactivity of labeled D-aptamers was 110,000-300,000 cpm/pmol. Labeled D-aptamers are incubated at 0.2 nM concentration in selection buffer (20 mM Tris, pH 7.4, 150 mM NaCl, 5 mM KCl, 1 mM $MgCl_2$, 1 mM $CaCl_2$, 0.1% Tween 20, 100 μg/ml essential fatty acid free bovine serum albumin, 200 μg/ml yeast RNA) together with varying amounts of D-CXCL8(C-bio) ranging from 0.0192 to 300 nM for 1.5-2 hours at 37° C. D-CXCL8(C-bio)/D-aptamer complexes are immobilized on NAag+ beads (Neutravidin agarose plus from Pierce Biotechnology, Rockford, USA) preequilibrated in selection buffer. After detaching the supernatant and appropriate washing, bead-bound radioactivity is measured in a scintillation counter (LS6500; Beckman Coulter, Fullerton, USA). The amount of immobilized, labeled D-aptamer (% of input) is plotted against the concentration of D-CXCL8(C-bio) and dissociation constants Kd are obtained by using software algorithms (GRAFIT; Erithacus Software; Surrey U.K.) assuming a 1:1 stoichiometry.

For the CXCL8 binding aptamers 315-H9-001 and 315-F8-001 Kd values of 1.7 nM and 0.8 nM were determined by direct pull-down assay, respectively.

Competition Pull-Down Assay for Ranking and Determination of Binding Constants of D-Aptamers Competition pull-down assays are used to compare affinities of different D-CXCL8(C-bio) binding D-aptamers. For this purpose, a reference D-aptamer is radioactively labeled (as described above) and incubated at 37° C. with D-CXCL8 (C-bio) in selection buffer at conditions that result in a non-saturated binding signal after immobilization on NAag+ and washing (e.g. 3 nM D-CXCL8(C-bio), 0.15 nM labeled D-aptamer). Addition of an excess amount of a non-labeled D-aptamer that competes with the labeled D-aptamer for binding to D-CXCL8(C-bio) results in a decreased in the amount of bead-bound, radioactivity after immobilization and washing. The degree of signal reduction depends on the amount and affinity of the non-labeled D-aptamer. Competition pull-down assays are used for ranking experiments and to determine dissociation constants (Kd) of selected D-aptamers. Dissociation constants Kd are determined by plotting the fraction (in %) of a labeled D-aptamer bound to D-CXCL8(C-bio) against the concentration of the non-labeled competitive D-aptamer. Data analyses were performed with GRAFIT.

The results of the pull-down binding assays are specified in Example 1 and shown in FIGS. 1, 2 and 3, wherein as labeled D-aptamer the CXCL8 nucleic acid 315-F8-001 was used.

EXAMPLE 4: SURFACE PLASMON RESONANCE (SPR) BINDING ASSAYS

Surface plasmon resonance measurements were performed on a Biacore 2000 instrument (GE Healthcare) set to a constant temperature of 25° C. or 37° C. Proteins was immobilized on CM4 sensor chips (GE Healthcare) by amine coupling. The sensor chip surface was activated by injection of a 1:1 mixture of 0.4 M EDC (1-ethyl-3-(3-dimethylaminopropyl) carbodiimide; GE) and 0.1 M NHS (N-hydroxysuccinimide; GE). The maximal observed response for covalently immobilized peptide or protein was about 500 RU. The flow cells were blocked with 1 M ethanolamine hydrochloride (GE, BR-1000-50). Non-covalently bound peptide or protein is also removed by this procedure. A flow cell with untreated dextran surface and a flow cell with ethanolamine-blocked surface served as controls. Prior to measurement, the sensor chip was primed twice with degassed physiological running buffer (20 mM Tris pH 7.4, 150 mM NaCl, 5 mM KCl, 1 mM $MgCl_2$ and 1 mM $CaCl_2$)) and underwent at least three injection and regeneration (5 M NaCl) cycles.

Binding affinities of L-aptamers were measured by injection of a concentration series of 1000, 500, 250, 125, 62.5, 31.3, 15.6, 7.8, 3.9, 1.95, 0.98, 0.49, 0.24, 0.12, 0.06 nM and recording of the binding event's association and dissociation phase. The resulting binding curves were fitted to a Langmuir 1:1 stoichiometric binding model to determine the binding kinetic rate constants (association constants ka; dissociation constant kd) which are used to calculate the dissociation constant (Kd=kd/ka). Data analysis were done with the BIAevaluation 3.1.1 software (BIACORE AB, Uppsala, Sweden) with a constant refractive index (RI) value and an initial mass transport coefficient kt of 1×10e7 ($RU \cdot M^{-1} s^{-1}$).

Selectivity of L-aptamer binding was evaluated by a competitive binding assays. For this purpose, human chemokines CXCL1, CXCL2, CXCL3, CXCL5, CXCL6, CXCL7, and CXCL8 (purchased from RnD Systems, PeproTech, or ProSpecTech) were individually injected at 40 nM along with the L-aptamer of CXCL8-binding nucleic acid 315-F8-002 (0.25 nM) to compete for binding of the L-aptamer to immobilized CXCL8. As a control, chemokines were injected in the absence of the L-aptamer to monitor for binding to the sensor chip dextran matrix or/and immobilized CXCL8. Binding of 315-F8-002 to immobilized CXCL8 was recorded at a predefined report point 240 s after the end of injection. Selected chemokines were immobilized and binding affinities of the L-aptamer of CXCL8-binding nucleic acid 315-F8-002 were determined as described above. The results of the SPR binding assays are specified in Example 1 and shown in FIGS. 2, 4, 5 and 6.

EXAMPLE 5: IN VITRO PHARMACOLOGY—CHEMOTAXIS ASSAY

The BA/F3 mouse pro-B cell line was stably transfected using a plasmid coding for the human CXCR2. For chemotaxis assays, recombinant CXCL8 (0.5 nM) was preincubated with the L-aptamer of CXCL8-binding nucleic acid 315-F8-002-PEG at indicated concentrations in HBH buffer (Hanks balanced salt solution (HBSS)+1 mg/ml BSA+20 mM HEPES) in the lower compartments of a 96-well Coming Transwell plate with 5 μm pores (Costar Coming, NY) at 37° C. for 20-30 minutes. CXCR2+ cells in HBH buffer were added to the upper compartments and could migrate at 37° C. for 3 hours. After removal of the upper compartments 50 μM resazurin (Sigma-Aldrich) in PBS was added to the lower compartments and incubated at 37° C. for 2.5 hours. Fluorescence was measured at 590 nm (excitation wavelength 544 nm). Background-corrected and normalized fluorescence values were plotted against L-aptamer concentration. Inhibitory constant $IC_{50}$ values (L-aptamer concentrations required for half-maximal inhibition) were determined with nonlinear regression (4 parameter fit) using Prism 5 software (GraphPad Software, San Diego, CA).

The results of the chemotaxis assays are specified in Example 1 and shown in FIG. 7.

EXAMPLE 6: CXCL8 BIOSENSOR

SPR-sensor chips coated with azide-terminated carbo nanomembrane were prepared and the CXCL8-binding L-aptamer 315-F8-002-DBCO (a DBCO-modified variant of 315-F8-002-Amino) was immobilised out of a 20 μM solution in 2 M NaCl on a flow cell of a commercial Biacore system (to about 1000 RU). As a reference, the non-functional L-aptamer (DBCO-modified reverse 315-F8-002-Amino), was immobilised to a similar amount on another flow cell. The surfaces were passivated by immobilising DBCO-modified linear methoxy-terminated polyethylene glycol (MW: 5 kDa). Injection of a concentration series of the analyte CXCL8 that was spiked into a standard sample buffer (Universal Transport Medium from Copan) with the addition of 0.1% (w/v) Tween20 showed a dose-dependent increase of the signal. The temperature of the measurement was 25° C., the flow was 30 pL/min and the running buffer was measurement buffer (20 mM Tris pH 7.4, 150 mM NaCl, 5 mM KCl, 1 mM $MgCl_2$, 1 mM $CaCl_2$, 0.1% (w/v) Tween20). The analyte was allowed to associate for 10 min followed by a dissociation time in measurement buffer of 2.5 min. The signal at the end of the dissociation phase was referenced by subtraction of the signal on the reference flow cell.

The results of the CXCL8 biosensor are specified in Example 1 and shown in FIG. 8.

EXAMPLE 7: SPR BINDING ASSAY FOR COMPARISON OF BINDING TO SOLUBLE CHEMOKINES

The inhibitory activity of an aptamer depends on its ability to bind to its target in solution. Here, a competitive SPR binding assay was used to determine the binding of the L aptamer of CXCL8-binding nucleic acid 315 F8 002 according to the present invention and the previously published aptamer 8A-35 (Sung, Biomaterials 2014) to soluble CXCL8 and CXCL1. For this purpose, SPR measurements were performed as described in Example 4 with CXCL8 being immobilized on a C1 sensor chip (GE Healthcare) by amine coupling. Binding of 315 F8 002 (3 nM) or 8A-35 (1.6 nM) to immobilized CXCL8 resulted in a binding response of approximately 20 response units. In 8A-35 binding assays, sensor chips were regenerated using 1M $CaCl_2$ solution. To evaluate the binding of both aptamers to their target in solution, soluble CXCL8 was concomitantly injected at equimolar concentration (1:1 ratio) or at 5-fold excess (1:5 ratio) to compete with aptamer binding to immobilized CXCL8. Binding of soluble CXCL1 was used as a control. All measurements were performed at 37° C. Binding responses to immobilized CXCL8 were recorded at 240 s after injection.

Binding of 315-F8-002 to immobilized CXCL8 was completely blocked (>90%) by an equimolar concentration of soluble CXCL8 (FIG. 9A). In contrast, binding of 8A 35 was only partially blocked by soluble CXCL8 at equimolar (ca. 30%) and at 5-fold excess concentration (ca. 45%) (FIG. 9B). This shows that 315-F8-002 has a higher binding affinity to soluble CXCL8 compared to 8A-35. A reduced binding affinity to soluble CXCL8 (compared surface immobilized CXCL8) may explain the poor inhibitory activity of 8A-358 observed in a CXCL8-induced neutrophil migration assay (Sung, Biomaterials 2014).

Soluble CXCL1 was used as a control as 315-F8-002 was shown to have no cross-reactivity to other ELR-positive chemokines (FIG. 6). In agreement, binding of 315-F8-002 was not blocked by soluble CXCL1 (FIG. 9A). Surprisingly, binding of 8A-358 was blocked by soluble CXCL1 with similar efficacy as by soluble CXCL8 (ca. 25% at equimolar and ca. 35% at 5-fold excess concentration) (FIG. 9B). This shows that 8A-35, in contrast to 315-F8-002, does not selectively bind to and prospectively inhibit CXCL8 in solution.

REFERENCES

The complete bibliographic data of the documents recited herein the disclosure of which is incorporated by reference is, if not indicated to the contrary, as follows.

Altschul S F, Gish W, Miller W, Myers E W, Lipman DJ (1990), Basic local alignment search tool. J Mol Biol. 215(3):403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res. 25(17):3389-402.

Bao, Z., et al. (2010), Humanized monoclonal antibody against the chemokine CXCL-8 (IL-8) effectively prevents acute lung injury. Int Immunopharmacol. 10(2): 259-63. Brand, H. K., et al. (2013), CD4+ T-cell counts and interleukin-8 and CCL-5 plasma concentrations discriminate disease severity in children with RSV infection. Pediatr Res. 73(2): 187-93.

Brat, D. J., A. C. Bellail, and E. G. Van Meir (2005), The role of interleukin-8 and its receptors in gliomagenesis and tumoral angiogenesis. Neuro Oncol. 7(2): 122-33.

Campbell, L. M., P. J. Maxwell, and D. J. Waugh (2013), Rationale and Means to Target Pro-Inflammatory Interleukin-8 (CXCL8) Signaling in Cancer. Pharmaceuticals (Basel). 6(8): 929-59.

Chen, Y., et al. (2012), Interleukin-8, a promising predictor for prognosis of pancreatic cancer. World J Gastroenterol. 18(10): 1123-9.

David, J. M., et al. (2016), The IL-8/IL-8R Axis: A Double Agent in Tumor Immune Resistance. Vaccines (Basel). 4(3): 22.

Fang, Q. I., et al. (2017), Increased CXCL8 Expression Is Negatively Correlated with the Overall Survival of Patients with ER-Negative Breast Cancer. Anticancer Res. 37(9): 4845-4852.

Feniger-Barish, R., et al. (1999), Differential modes of regulation of cxc chemokine-induced internalization and recycling of human CXCR1 and CXCR2. Cytokine. 11(12): 996-1009.

Garau, A., et al. (2005), Neuroprotection with the CXCL8 inhibitor repertaxin in transient brain ischemia. Cytokine. 30(3): 125-31.

Ginestier, C., et al. (2010), CXCR1 blockade selectively targets human breast cancer stem cells in vitro and in xenografts. J Clin Invest. 120(2): 485-97.

Ha, H., B. Debnath, and N. Neamati (2017), Role of the CXCL8-CXCRT/2 Axis in Cancer and Inflammatory Diseases. Theranostics. 7(6): 1543-1588.

Harada, A., et al. (1994), Essential involvement of interleukin-8 (IL-8) in acute inflammation. J Leukoc Biol. 56(5): 559-64.

Highfill, S. L., et al. (2014), Disruption of CXCR2-mediated MDSC tumor trafficking enhances anti-PD1 efficacy. Sci Transl Med. 6(237): 237ra67.

Jamal, R., et al. (2017), Peripheral and local predictive immune signatures identified in a phase II trial of ipilimumab with carboplatin/paclitaxel in unresectable stage III or stage IV melanoma. J Immunother Cancer. 5(1): 83.

Klussmann S. (2006). "The Aptamer Handbook—Functional Oligonucleotides and their Applications." Edited by S. Klussmann. WILEY-VCH, Weinheim, Germany, ISBN 3-527-31059-2

Koch, A. E., et al. (1992), Interleukin-8 as a macrophage-derived mediator of angiogenesis. Science. 258(5089): 1798-801.

Kratschmer, C. and M. Levy, Effect of Chemical Modifications on Aptamer Stability in Serum. Nucleic Acid Ther, 2017. 27(6): p. 335-344.

Kusser W (2000). J Biotechnol 74:27-38

Li, A., et al. (2005), Autocrine role of interleukin-8 in induction of endothelial cell proliferation, survival, migration and MMP-2 production and angiogenesis. Angiogenesis. 8(1): 63-71.

Liu, Q., et al. (2016), The CXCL8-CXCR1/2 pathways in cancer. Cytokine Growth Factor Rev. 31: 61-71.

Ludwig, H., et al. (2017), Olaptesed pegol, an anti-CXCL12/SDF-1 Spiegelmer, alone and with bortezomib-dexamethasone in relapsed/refractory multiple myeloma: a Phase IIa Study. Leukemia. 31(4): 997-1000.

Maxwell, P. J., et al. (2013), Potentiation of inflammatory CXCL8 signalling sustains cell survival in PTEN-deficient prostate carcinoma. Eur Urol. 64(2): 177-88.

Maxwell, P. J., et al. (2014), Tumor-derived CXCL8 signaling augments stroma-derived CCL2-promoted proliferation and CXCL12-mediated invasion of PTEN-deficient prostate cancer cells. Oncotarget. 5(13): 4895-4908.

McGinnis S, Madden TL (2004) BLAST: at the core of a powerful and diverse set of sequence analysis tools. Nucleic Acids Res. 32(Web Server issue):W20-5.

Menne, J., et al. (2017), C-C motif-ligand 2 inhibition with emapticap pegol (NOX-E36) in type 2 diabetic patients with albuminuria. Nephrol Dial Transplant. 32(2): 307-315.

Merritt, W. M., et al. (2008), Effect of interleukin-8 gene silencing with liposome-encapsulated small interfering RNA on ovarian cancer cell growth. J Natl Cancer Inst. 100(5): 359-72.

Morris, A. C., et al. (2009), Diagnostic importance of pulmonary interleukin-1! and interleukin-8 in ventilator-associated pneumonia. Thorax. thx. 2009.122291.

Needleman & Wunsch (1970) A general method applicable to the search for similarities in the amino acid sequence of two proteins. J Mol Biol. 48(3):443-53.

Oberthur, D., et al. (2015), Crystal structure of a mirror-image L-RNA aptamer (Spiegelmer) in complex with the natural L-protein target CCL2. Nat Commun. 6: 6923.

Pearson & Lipman (1988) Improved tools for biological sequence comparison. Proc. Nat'l. Acad. Sci. USA 85: 2444

Russo, R. C., et al. (2014), The CXCL8/IL-8 chemokine family and its receptors in inflammatory diseases. Expert Rev Clin Immunol. 10(5): 593-619.

Sanmamed, M. F., et al. (2014), Serum interleukin-8 reflects tumor burden and treatment response across malignancies of multiple tissue origins. Clin Cancer Res. 20(22): 5697-707.

Sawant, K. V., et al. (2016), Chemokine CXCL1 mediated neutrophil recruitment: Role of glycosaminoglycan interactions. Sci Rep. 6: 33123.

Shahzad, A., et al. (2010), Interleukin 8 (IL-8) - a universal biomarker?Int Arch Med. 3: p. 11.

Skov, L., et al. (2008), IL-8 as antibody therapeutic target in inflammatory diseases: reduction of clinical activity in palmoplantar pustulosis. J Immunol. 181(1): 669-79.

Smith & Waterman (1981) Adv. Appl. Math. 2: 482

Steele, C. W., et al. (2016), CXCR2 Inhibition Profoundly Suppresses Metastases and Augments Immunotherapy in Pancreatic Ductal Adenocarcinoma. Cancer Cell. 29(6): 832-45.

Sung, H. J., et al., Inhibition of human neutrophil activity by an RNA aptamer bound to interleukin-8. Biomaterials, 2014. 35(1): p. 578-89.

Venkatesan N, Kim S J, Kim BH (2003) Novel phosphoramidite building blocks in synthesis and applications toward modified oligonucleotides. Curr Med Chem 10(19): 1973-1991

Visvader, J. E. and G. J. Lindeman (2008), Cancer stem cells in solid tumours: accumulating evidence and unresolved questions. Nat Rev Cancer. 8(10): 755-68.

Wang, C., et al. (2016), CXCL13, CXCL10 and CXCL8 as Potential Biomarkers for the Diagnosis of Neurosyphilis Patients. Sci Rep. 6: 33569.

Wincott F, DiRenzo A, Shaffer C, Grimm S, Tracz D, Workman C, Sweedler D, Gonzalez C, Scaringe S, and Usman N (1995). Synthesis, deprotection, analysis and purification of RNA and ribosomes. Nucleic Acids Res. 23:2677-2684.

Xu, L. and I. J. Fidler (2000), Interleukin 8: an autocrine growth factor for human ovarian cancer. Oncol Res. 12(2): 97-106.

Yao, R., et al. (2015), Diagnostic performance of interleukin-6 and interleukin-8 for bacterial meningitis: a meta-analysis. Int J Clin Exp Med. 8(5): 7059-68.

Zhou, M., et al. (2015), Interleukin-8 for diagnosis of neonatal sepsis: a meta-analysis. PLoS One. 10(5): e0127170.

The project leading to this application has received funding from the European Union's Horizon 2020 research and innovation programme under grant agreement No 634415.

The invention claimed is:

1. An L-nucleic acid molecule that binds human CXCL8 comprising one of SEQ ID NOs:14-26, and 39-44.

2. The L-nucleic acid molecule of claim 1, wherein said L-nucleic acid molecule consists of ribonucleotides.

3. The L-nucleic acid molecule of claim 1, wherein said L-nucleic acid molecule comprises a modification group, wherein said modification group comprises a polyethylene glycol.

4. The L- nucleic acid molecule of claim 3, wherein the modification group is selected from the group consisting of a linear polyethylene glycol and a branched polyethylene glycol.

5. The L-nucleic acid molecule of claim 3, wherein said polyethylene glycol comprises a molecular weight of about 40,000 Da.

6. The L-nucleic acid molecule of claim 1, wherein said L-nucleic acid molecule comprises a modification group, wherein said modification group immobilizes said L-nucleic acid molecule.

7. The L-nucleic acid molecule of claim 1, wherein said L-nucleic acid molecule comprises a modification group, wherein said modification group is detectable.

8. The L- nucleic acid molecule of claim 1 comprising the nucleotide sequence of SEQ ID NO:17.

9. The L-nucleic acid molecule of claim 8, wherein said L-nucleic acid molecule comprises a modification group comprising a polyethylene glycol.

10. The L-nucleic acid molecule of claim 9, wherein said polyethylene glycol comprises a molecular weight of about 40,000 Da.

11. The L-nucleic acid molecule of claim 9, wherein said modification group comprises a linear polyethylene glycol or a branched polyethylene glycol.

12. The L- nucleic acid molecule of claim 1, comprising the nucleotide sequence of SEQ ID NO:20.

13. The L-nucleic acid molecule of claim 12, wherein said L-nucleic acid molecule comprises a modification group comprising a polyethylene glycol.

14. The L-nucleic acid molecule of claim 13, wherein said polyethylene glycol comprises a molecular weight of about 40,000 Da.

15. The L-nucleic acid molecule of claim 13, wherein said modification group comprises a linear polyethylene glycol or a branched polyethylene glycol.

16. A pharmaceutical composition comprising said L-nucleic acid molecule as defined in claim 1 and optionally a pharmaceutically acceptable excipient, a pharmaceutically acceptable carrier or a pharmaceutically active agent.

17. A complex comprising said L-nucleic acid molecule of claim 1 and CXCL8.

18. A kit for the detection of CXCL8, comprising the L-nucleic acid molecule of claim 1, and at least an instruction leaflet or a reaction vessel.

19. A method for the detection of the L-nucleic acid as defined in claim 1 in a sample, wherein the method comprises the steps of:
   a) providing a capture probe, wherein the capture probe is at least partially complementary to a first part of the L-nucleic acid molecule as defined in claim 1 and a detection probe, wherein the detection probe is at least partially complementary to a second part of the L-nucleic acid molecule as defined in claim 1, or, alternatively, the capture probe is at least partially complementary to a second part of the L-nucleic acid molecule as defined in claim 1 and the detection probe is at least partially complementary to a first part of the L-nucleic acid molecule as defined in claim 1;
   b) adding the capture probe and the detection probe separately or combined to a sample containing the L-nucleic acid molecule as defined in claim 1 or presumed to contain the L-nucleic acid molecule as defined in claim 1;
   c) allowing the capture probe and the detection probe to react either simultaneously or in any order sequentially with the L-nucleic acid molecule as defined in claim 1 or part thereof,
   d) optionally detecting whether or not the capture probe is hybridized to the L-nucleic acid molecule as defined in claim 1 provided in step a); and
   e) detecting the complex formed in step c) consisting of the L-nucleic acid molecule as defined in claim 1 and the capture probe and the detection probe.

20. A method for the detection of CXCL8 comprising the steps of:
   a) providing a sample with unknown concentration of CXCL8;
   b) bringing the sample or a dilution thereof in contact with the L-nucleic acid as defined in claim 7; and
   c) measuring the detectable modification group;
   d) optionally, comparing signal from said detectable modification group with signal of a reference; or
   e) optionally, comparing signal from said detectable modification group with signal of a sample of known CXCL8 concentration.

21. The method of claim 1, comprising step e).

* * * * *

SEQUENCE LISTING

<160> NUMBER OF SEQ ID NOS: 45

<210> SEQ ID NO 1
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(77)
<223> OTHER INFORMATION: D-amino acid
<220> FEATURE:
<221> NAME/KEY: MISC_FEATURE
<222> LOCATION: (77)..(77)
<223> OTHER INFORMATION: biotin attached

<400> SEQUENCE: 1

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser
65                  70                  75

<210> SEQ ID NO 2
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: CXCL8

<400> SEQUENCE: 2

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser
65                  70                  75

<210> SEQ ID NO 3
<211> LENGTH: 45
<212> TYPE: RNA
<213> ORGANISM: Artificial Sequence
<220> FEATURE:
<223> OTHER INFORMATION: Synthetic

<400> SEQUENCE: 3
gcugacggaa guacguggaa agccaaugag uguguccegg ucagc            45

<210> SEQ ID NO 4
<211> LENGTH: 45
<212> TYPE: RNA
<213> ORGANISM: Artificial Sequence

```
<220> FEATURE:
<223> OTHER INFORMATION: Syntetic

<400> SEQUENCE: 4
gcugacggaa guacguggaa agccgaugag ugugucccgg ugagc          45

<210> SEQ ID NO 5
<211> LENGTH: 44
<212> TYPE: RNA
<213> ORGANISM: Artificial Sequence
<220> FEATURE:
<223> OTHER INFORMATION: Synthetic

<400> SEQUENCE: 5
gcugacggaa guacguggaa agccgaaagu gugucccggu cagc            44

<210> SEQ ID NO 6
<211> LENGTH: 42
<212> TYPE: RNA
<213> ORGANISM: Artificial Sequence
<220> FEATURE:
<223> OTHER INFORMATION: Synthetic

<400> SEQUENCE: 6
cugacggaag uacguggaaa gccgaaagug ugucccgguc ag              42

<210> SEQ ID NO 7
<211> LENGTH: 40
<212> TYPE: RNA
<213> ORGANISM: Artificial Sequence
<220> FEATURE:
<223> OTHER INFORMATION: Sythetic

<400> SEQUENCE: 7
ugacggaagu acguggaaag ccgaaagugu gucccgguca                 40

<210> SEQ ID NO 8
<211> LENGTH: 38
<212> TYPE: RNA
<213> ORGANISM: Artificial Sequence
<220> FEATURE:
<223> OTHER INFORMATION: Synthetic

<400> SEQUENCE: 8
gacggaagua cguggaaagc cgaaagugug ucccgguc                   38

<210> SEQ ID NO 9
<211> LENGTH: 42
<212> TYPE: RNA
<213> ORGANISM: Artificial Sequence
<220> FEATURE:
<223> OTHER INFORMATION: Synthetic

<400> SEQUENCE: 9
gugacggaag uacguggaaa gccgaaagug ugucccgguc ac              42

<210> SEQ ID NO 10
<211> LENGTH: 40
<212> TYPE: RNA
<213> ORGANISM: Artificial Sequence
<220> FEATURE:
<223> OTHER INFORMATION: Synthetic

<400> SEQUENCE: 10
ggacggaagu acguggaaag ccgaaagugu gucccggucc                 40
```

<210> SEQ ID NO 11
<211> LENGTH: 40
<212> TYPE: RNA
<213> ORGANISM: Artificial Sequence
<220> FEATURE:
<223> OTHER INFORMATION: Synthetic

<400> SEQUENCE: 11
gcacggaagu acguggaaag ccgaaagugu gucccggugc           40

<210> SEQ ID NO 12
<211> LENGTH: 40
<212> TYPE: RNA
<213> ORGANISM: Artificial Sequence
<220> FEATURE:
<223> OTHER INFORMATION: Synthetic

<400> SEQUENCE: 12
ggucggaagu acguggaaag ccgaaagugu gucccggacc           40

<210> SEQ ID NO 13
<211> LENGTH: 40
<212> TYPE: RNA
<213> ORGANISM: Artificial Sequence
<220> FEATURE:
<223> OTHER INFORMATION: Synthetic

<400> SEQUENCE: 13
uggcggaagu acguggaaag ccgaaagugu gucccggcca           40

<210> SEQ ID NO 14
<211> LENGTH: 45
<212> TYPE: RNA
<213> ORGANISM: Artificial Sequence
<220> FEATURE:
<223> OTHER INFORMATION: Synthetic

<400> SEQUENCE: 14
gcugacggaa guacguggaa agccaaugag uguucccggg ucagc           45

<210> SEQ ID NO 15
<211> LENGTH: 45
<212> TYPE: RNA
<213> ORGANISM: Artificial Sequence
<220> FEATURE:
<223> OTHER INFORMATION: Synthetic

<400> SEQUENCE: 15
gcugacggaa guacguggaa agccgaugag uguucccggg ugagc           45

<210> SEQ ID NO 16
<211> LENGTH: 44
<212> TYPE: RNA
<213> ORGANISM: Artificial Sequence
<220> FEATURE:
<223> OTHER INFORMATION: Synthetic

<400> SEQUENCE: 16
gcugacggaa guacguggaa agccgaaagu gugucccggu cagc           44

<210> SEQ ID NO 17
<211> LENGTH: 42
<212> TYPE: RNA
<213> ORGANISM: Artificial Sequence
<220> FEATURE:
<223> OTHER INFORMATION: Synthetic

<400> SEQUENCE: 17
cugacggaag uacguggaaa gccgaaagug ugucccgguc ag            42

<210> SEQ ID NO 18
<211> LENGTH: 40
<212> TYPE: RNA
<213> ORGANISM: Artificial Sequence
<220> FEATURE:
<223> OTHER INFORMATION: Synthetic

<400> SEQUENCE: 18
ugacggaagu acguggaaag ccgaaagugu gucccgguca              40

<210> SEQ ID NO 19
<211> LENGTH: 38
<212> TYPE: RNA
<213> ORGANISM: Artificial Sequence
<220> FEATURE:
<223> OTHER INFORMATION: Synthetic

<400> SEQUENCE: 19
gacggaagua cguggaaagc cgaaagugug ucccgguc                38

<210> SEQ ID NO 20
<211> LENGTH: 42
<212> TYPE: RNA
<213> ORGANISM: Artificial Sequence
<220> FEATURE:
<223> OTHER INFORMATION: Synthetic

<400> SEQUENCE: 20
gugacggaag uacguggaaa gccgaaagug ugucccgguc ac            42

<210> SEQ ID NO 21
<211> LENGTH: 40
<212> TYPE: RNA
<213> ORGANISM: Artificial Sequence
<220> FEATURE:
<223> OTHER INFORMATION: Synthetic

<400> SEQUENCE: 21
ggacggaagu acguggaaag ccgaaagugu gucccggucc              40

<210> SEQ ID NO 22
<211> LENGTH: 40
<212> TYPE: RNA
<213> ORGANISM: Artificial Sequence
<220> FEATURE:
<223> OTHER INFORMATION: Synthetic

<400> SEQUENCE: 22
gcacggaagu acguggaaag ccgaaagugu gucccggugc              40

<210> SEQ ID NO 23
<211> LENGTH: 40
<212> TYPE: RNA
<213> ORGANISM: Artificial Sequence
<220> FEATURE:
<223> OTHER INFORMATION: Synthetic

<400> SEQUENCE: 23
ggucggaagu acguggaaag ccgaaagugu gucccggacc              40

<210> SEQ ID NO 24

```
<211> LENGTH: 40
<212> TYPE: RNA
<213> ORGANISM: Artificial Sequence
<220> FEATURE:
<223> OTHER INFORMATION: Synthetic

<400> SEQUENCE: 24
uggcggaagu acguggaaag ccgaaagugu gucccggcca                              40

<210> SEQ ID NO 25
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PEG linked through aminohexyl linker to 5' end

<400> SEQUENCE: 25
cugacggaag uacguggaaa gccgaaagug ugucccgguc ag                           42

<210> SEQ ID NO 26
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: aminohexyl linker attached to 5' end

<400> SEQUENCE: 26
cugacggaag uacguggaaa gccgaaagug ugucccgguc ag                           42

<210> SEQ ID NO 27
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: U is U or absent

<400> SEQUENCE: 27
ggaaguacgu ggaaagccra uraguguguc ccg                                    33

<210> SEQ ID NO 28
<211> LENGTH: 33
<212> TYPE: RNA
<213> ORGANISM: Artificial Sequence
<220> FEATURE:
<223> OTHER INFORMATION: Synthetic

<400> SEQUENCE: 28
ggaaguacgu ggaaagccaa ugaguguguc ccg                                    33

<210> SEQ ID NO 29
<211> LENGTH: 33
<212> TYPE: RNA
<213> ORGANISM: Artificial Sequence
<220> FEATURE:
<223> OTHER INFORMATION: Synthetic

<400> SEQUENCE: 29
ggaaguacgu ggaaagccga ugaguguguc ccg                                    33
```

<210> SEQ ID NO 30
<211> LENGTH: 32
<212> TYPE: RNA
<213> ORGANISM: Artificial Sequence
<220> FEATURE:
<223> OTHER INFORMATION: Synthetic

<400> SEQUENCE: 30
ggaaguacgu ggaaagccga aaguguguccc cg                                32

<210> SEQ ID NO 31
<211> LENGTH: 42
<212> TYPE: RNA
<213> ORGANISM: Artificial Sequence
<220> FEATURE:
<223> OTHER INFORMATION: Synthetic

<400> SEQUENCE: 31
gacuggcccu gugugaaagc cgaaaggugc augaaggcag uc                      42

<210> SEQ ID NO 32
<211> LENGTH: 73
<212> TYPE: PRT
<213> ORGANISM: Homo sapiens
<220> FEATURE:
<221> NAME/KEY: MISC_FEATURE
<222> LOCATION: (1)..(73)
<223> OTHER INFORMATION: CXCL1

<400> SEQUENCE: 32

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser Asn
65                  70

<210> SEQ ID NO 33
<211> LENGTH: 73
<212> TYPE: PRT
<213> ORGANISM: Homo sapiens
<220> FEATURE:
<221> NAME/KEY: MISC_FEATURE
<222> LOCATION: (1)..(73)
<223> OTHER INFORMATION: CXCL2

<400> SEQUENCE: 33

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
            20                  25                  30

Pro His Cys Ala Gln Thr Glu Val Ile Ala Thr Leu Lys Asn Gly Gln
        35                  40                  45

Lys Ala Cys Leu Asn Pro Ala Ser Pro Met Val Lys Lys Ile Ile Glu
    50                  55                  60

Lys Met Leu Lys Asn Gly Lys Ser Asn
65                  70

```
<210> SEQ ID NO 34
<211> LENGTH: 73
<212> TYPE: PRT
<213> ORGANISM: Homo sapiens
<220> FEATURE:
<221> NAME/KEY: MISC_FEATURE
<222> LOCATION: (1)..(73)
<223> OTHER INFORMATION: CXCL3

<400> SEQUENCE: 34

Ala Ser Val Val Thr Glu Leu Arg Cys Gln Cys Leu Gln Thr Leu Gln
1               5                   10                  15

Gly Ile His Leu Lys Asn Ile Gln Ser Val Asn Val Arg Ser Pro Gly
            20                  25                  30

Pro His Cys Ala Gln Thr Glu Val Ile Ala Thr Leu Lys Asn Gly Lys
        35                  40                  45

Lys Ala Cys Leu Asn Pro Ala Ser Pro Met Val Gln Lys Ile Ile Glu
    50                  55                  60

Lys Ile Leu Asn Lys Gly Ser Thr Asn
65                  70

<210> SEQ ID NO 35
<211> LENGTH: 78
<212> TYPE: PRT
<213> ORGANISM: Homo sapiens
<220> FEATURE:
<221> NAME/KEY: MISC_FEATURE
<222> LOCATION: (1)..(78)
<223> OTHER INFORMATION: CXCL5

<400> SEQUENCE: 35

Ala Gly Pro Ala Ala Ala Val Leu Arg Glu Leu Arg Cys Val Cys Leu
1               5                   10                  15

Gln Thr Thr Gln Gly Val His Pro Lys Met Ile Ser Asn Leu Gln Val
            20                  25                  30

Phe Ala Ile Gly Pro Gln Cys Ser Lys Val Glu Val Val Ala Ser Leu
        35                  40                  45

Lys Asn Gly Lys Glu Ile Cys Leu Asp Pro Glu Ala Pro Phe Leu Lys
    50                  55                  60

Lys Val Ile Gln Lys Ile Leu Asp Gly Gly Asn Lys Glu Asn
65                  70                  75

<210> SEQ ID NO 36
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: CXCL6

<400> SEQUENCE: 36

Gly Pro Val Ser Ala Val Leu Thr Glu Leu Arg Cys Thr Cys Leu Arg
1               5                   10                  15

Val Thr Leu Arg Val Asn Pro Lys Thr Ile Gly Lys Leu Gln Val Phe
            20                  25                  30

Pro Ala Gly Pro Gln Cys Ser Lys Val Glu Val Val Ala Ser Leu Lys
        35                  40                  45

Asn Gly Lys Gln Val Cys Leu Asp Pro Glu Ala Pro Phe Leu Lys Lys
    50                  55                  60

Val Ile Gln Lys Ile Leu Asp Ser Gly Asn Lys Lys Asn
```

<210> SEQ ID NO 37
<211> LENGTH: 94
<212> TYPE: PRT
<213> ORGANISM: Homo sapiens
<220> FEATURE:
<221> NAME/KEY: MISC_FEATURE
<222> LOCATION: (1)..(94)
<223> OTHER INFORMATION: CXCL7

<400> SEQUENCE: 37

```
Ser Ser Thr Lys Gly Gln Thr Lys Arg Asn Leu Ala Lys Gly Lys Glu
1               5                   10                  15

Glu Ser Leu Asp Ser Asp Leu Tyr Ala Glu Leu Arg Cys Met Cys Ile
            20                  25                  30

Lys Thr Thr Ser Gly Ile His Pro Lys Asn Ile Gln Ser Leu Glu Val
        35                  40                  45

Ile Gly Lys Gly Thr His Cys Asn Gln Val Glu Val Ile Ala Thr Leu
    50                  55                  60

Lys Asp Gly Arg Lys Ile Cys Leu Asp Pro Asp Ala Pro Arg Ile Lys
65                  70                  75                  80

Lys Ile Val Gln Lys Lys Leu Ala Gly Asp Glu Ser Ala Asp
                85                  90
```

<210> SEQ ID NO 38
<211> LENGTH: 68
<212> TYPE: PRT
<213> ORGANISM: Homo sapiens
<220> FEATURE:
<221> NAME/KEY: MISC_FEATURE
<222> LOCATION: (1)..(68)
<223> OTHER INFORMATION: CCL5

<400> SEQUENCE: 38

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65
```

<210> SEQ ID NO 39
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(42)
<223> OTHER INFORMATION: PEG attached through aminohexyl linker

<400> SEQUENCE: 39
cugacggaag uacguggaaa gccgaaagug ugucccgguc ag          42

<210> SEQ ID NO 40
<211> LENGTH: 42
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(42)
<223> OTHER INFORMATION: Aminohexyl linker attached

<400> SEQUENCE: 40
cugacggaag uacguggaaa gccgaaagug ugucccgguc ag                           42

<210> SEQ ID NO 41
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: PEG attached through aminohexal linker

<400> SEQUENCE: 41
gugacggaag uacguggaaa gccgaaagug ugucccgguc ac                           42

<210> SEQ ID NO 42
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Aminohexal linker attached

<400> SEQUENCE: 42
gugacggaag uacguggaaa gccgaaagug ugucccgguc ac                           42

<210> SEQ ID NO 43
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(42)
<223> OTHER INFORMATION: PEG attached through aminohexyl linker

<400> SEQUENCE: 43
gugacggaag uacguggaaa gccgaaagug ugucccgguc ac                           42

<210> SEQ ID NO 44
<211> LENGTH: 42
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(42)
<223> OTHER INFORMATION: Aminohexyl linker

<400> SEQUENCE: 44
gugacggaag uacguggaaa gccgaaagug ugucccgguc ac                           42

<210> SEQ ID NO 45
<211> LENGTH: 35
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: All C are 2' fluoro-C
<220> FEATURE:
<221> NAME/KEY: misc_feature
<223> OTHER INFORMATION: All U are 2' fluoro-U

<400> SEQUENCE: 45
gggggcuuau cauuccauuu aguguuauga uaacc                                   35
```